United States Patent [19]

Hammond et al.

[11] Patent Number: 5,939,384
[45] Date of Patent: *Aug. 17, 1999

[54] CYCLOHEXAPEPTIDYL PROPANOLAMINE COMPOUNDS

[75] Inventors: Milton L. Hammond, Somerville; Robert A. Zambias, Springfield, both of N.J.

[73] Assignee: Merck & Co., Inc., Rahway, N.J.

[ * ] Notice: This patent is subject to a terminal disclaimer.

[21] Appl. No.: 07/936,561

[22] Filed: Sep. 3, 1992

Related U.S. Application Data

[63] Continuation-in-part of application No. 07/771,017, Oct. 1, 1991, abandoned.

[51] Int. Cl.$^6$ .............................. A61K 38/12; C07K 7/54
[52] U.S. Cl. ............................ 514/11; 514/9; 514/2; 530/317; 530/318
[58] Field of Search ............... 514/11, 9, 2; 530/317, 530/318; 930/190, 200, 270, DIG. 546; 435/71.3, 71.1

[56] References Cited

U.S. PATENT DOCUMENTS

| | | | |
|---|---|---|---|
| 4,173,629 | 11/1979 | Dreyfuss et al. | 514/9 |
| 4,287,120 | 9/1981 | Abbott et al. | 530/317 |
| 4,293,485 | 10/1981 | Debono | 530/317 |
| 4,293,489 | 10/1981 | Debono | 530/317 |
| 4,320,054 | 3/1982 | Abbott et al. | 530/317 |
| 4,931,352 | 6/1990 | Fromtling et al. | 435/71.3 |
| 4,968,608 | 11/1990 | Giacobbe et al. | 435/71 |
| 5,021,341 | 6/1991 | Giacobbe et al. | 435/71.1 |
| 5,021,403 | 6/1991 | Sesin et al. | 514/9 |
| 5,166,135 | 11/1992 | Schmatz | 514/11 |

FOREIGN PATENT DOCUMENTS

| | | |
|---|---|---|
| 851310 | 8/1977 | Belgium . |
| 859067 | 3/1978 | Belgium . |
| 0 447 186 | 3/1991 | European Pat. Off. . |
| 0 459 564 | 5/1991 | European Pat. Off. . |
| 0 486 011A2 | 5/1992 | European Pat. Off. . |

OTHER PUBLICATIONS

Abstracts of the Belgiam Pats. 851,310 and 859,067.
The Merck Manual of Diagnosis and Therapy, p. 881, (1966).

*Primary Examiner*—Ponnathapura Achutamurthy
*Assistant Examiner*—T. D. Wessendorf
*Attorney, Agent, or Firm*—Elliott Korsen; Mark R. Daniel

[57] ABSTRACT

Certain propanolamine compounds which have a cyclohexapeptidyl nucleus and which are found to have extremely active antibiotic activity with physical properties suitable for direct use in therapeutic compositions are described. A novel process for their preparation is also described.

10 Claims, No Drawings

```
                         SEQUENCE LISTING (1) GENERAL INFORMATION:

(iii) NUMBER OF SEQUENCES: 42

(2) INFORMATION FOR SEQ ID NO: 1:

(i) SEQUENCE CHARACTERISTICS:
        (A) LENGTH: 6
        (B) TYPE: AMINO ACID
        (C) STRANDEDNESS: Not Relevant
        (D) TOPOLOGY: CIRCULAR (ii) MOLECULE TYPE:
        (A) DESCRIPTION: PEPTIDE (xi) SEQUENCE DESCRIPTION: SEQ ID NO: 1:

Xaa Thr Xaa Xaa Xaa Xaa
        1               5

(2) INFORMATION FOR SEQ ID NO: 2:

(i) SEQUENCE CHARACTERISTICS:
        (A) LENGTH: 6
        (B) TYPE: AMINO ACID
        (C) STRANDEDNESS: Not Relevant
        (D) TOPOLOGY: CIRCULAR (ii) MOLECULE TYPE:
        (A) DESCRIPTION: PEPTIDE (xi) SEQUENCE DESCRIPTION: SEQ ID NO: 2:

Xaa Thr Xaa Xaa Xaa Xaa
        1               5

(2) INFORMATION FOR SEQ ID NO: 3:

(i) SEQUENCE CHARACTERISTICS:
        (A) LENGTH: 6
        (B) TYPE: AMINO ACID
        (C) STRANDEDNESS: Not Relevant
        (D) TOPOLOGY: CIRCULAR (ii) MOLECULE TYPE:
        (A) DESCRIPTION: PEPTIDE (xi) SEQUENCE DESCRIPTION: SEQ ID NO: 3:

Xaa Ser Xaa Xaa Xaa Xaa
        1               5
```

(2) INFORMATION FOR SEQ ID NO: 4:

(i) SEQUENCE CHARACTERISTICS:
        (A) LENGTH: 6
        (B) TYPE: AMINO ACID
        (C) STRANDEDNESS: Not Relevant
        (D) TOPOLOGY: CIRCULAR (ii) MOLECULE TYPE:
        (A) DESCRIPTION: PEPTIDE (xi) SEQUENCE DESCRIPTION: SEQ ID NO: 4:

Xaa Thr Xaa Xaa Xaa Xaa
     1          5

(2) INFORMATION FOR SEQ ID NO: 5:

(i) SEQUENCE CHARACTERISTICS:
        (A) LENGTH: 6
        (B) TYPE: AMINO ACID
        (C) STRANDEDNESS: Not Relevant
        (D) TOPOLOGY: CIRCULAR (ii) MOLECULE TYPE:
        (A) DESCRIPTION: PEPTIDE (xi) SEQUENCE DESCRIPTION: SEQ ID NO: 5:

Xaa Thr Xaa Xaa Xaa Xaa
     1          5

(2) INFORMATION FOR SEQ ID NO: 6:

(i) SEQUENCE CHARACTERISTICS:
        (A) LENGTH: 6
        (B) TYPE: AMINO ACID
        (C) STRANDEDNESS: Not Relevant
        (D) TOPOLOGY: CIRCULAR (ii) MOLECULE TYPE:
        (A) DESCRIPTION: PEPTIDE (xi) SEQUENCE DESCRIPTION: SEQ ID NO: 6:

Xaa Thr Xaa Xaa Xaa Xaa
     1          5

(2) INFORMATION FOR SEQ ID NO: 7:

(i) SEQUENCE CHARACTERISTICS:
        (A) LENGTH: 6
        (B) TYPE: AMINO ACID
        (C) STRANDEDNESS: Not Relevant
        (D) TOPOLOGY: CIRCULAR (ii) MOLECULE TYPE:
        (A) DESCRIPTION: PEPTIDE (xi) SEQUENCE DESCRIPTION: SEQ ID NO: 7:

Xaa Thr Xaa Xaa Xaa Xaa
     1          5

(2) INFORMATION FOR SEQ ID NO: 8:

(i) SEQUENCE CHARACTERISTICS:
        (A) LENGTH: 6
        (B) TYPE: AMINO ACID
        (C) STRANDEDNESS: Not Relevant
        (D) TOPOLOGY: CIRCULAR (ii) MOLECULE TYPE:
        (A) DESCRIPTION: PEPTIDE (xi) SEQUENCE DESCRIPTION: SEQ ID NO: 8:

```
        Xaa Thr Xaa Xaa Xaa Xaa
        1               5

(2) INFORMATION FOR SEQ ID NO: 9:

(i) SEQUENCE CHARACTERISTICS:
         (A) LENGTH: 6
         (B) TYPE: AMINO ACID
         (C) STRANDEDNESS: Not Relevant
         (D) TOPOLOGY: CIRCULAR (ii) MOLECULE TYPE:
         (A) DESCRIPTION: PEPTIDE (xi) SEQUENCE DESCRIPTION: SEQ ID NO: 9:

Xaa Thr Xaa Xaa Xaa Xaa
        1               5

(2) INFORMATION FOR SEQ ID NO: 10:

(i) SEQUENCE CHARACTERISTICS:
         (A) LENGTH: 6
         (B) TYPE: AMINO ACID
         (C) STRANDEDNESS: Not Relevant
         (D) TOPOLOGY: CIRCULAR (ii) MOLECULE TYPE:
         (A) DESCRIPTION: PEPTIDE (xi) SEQUENCE DESCRIPTION: SEQ ID NO: 10:

Xaa Ser Xaa Xaa Xaa Xaa
        1               5

(2) INFORMATION FOR SEQ ID NO: 11:

(i) SEQUENCE CHARACTERISTICS:
         (A) LENGTH: 6
         (B) TYPE: AMINO ACID
         (C) STRANDEDNESS: Not Relevant
         (D) TOPOLOGY: CIRCULAR (ii) MOLECULE TYPE:
         (A) DESCRIPTION: PEPTIDE (xi) SEQUENCE DESCRIPTION: SEQ ID NO: 11:

Xaa Ser Xaa Xaa Xaa Xaa
        1               5

(2) INFORMATION FOR SEQ ID NO: 12:

(i) SEQUENCE CHARACTERISTICS:
         (A) LENGTH: 6
         (B) TYPE: AMINO ACID
         (C) STRANDEDNESS: Not Relevant
         (D) TOPOLOGY: CIRCULAR (ii) MOLECULE TYPE:
         (A) DESCRIPTION: PEPTIDE (xi) SEQUENCE DESCRIPTION: SEQ ID NO: 12:

Xaa Thr Xaa Xaa Xaa Xaa
        1               5

(2) INFORMATION FOR SEQ ID NO: 13:

(i) SEQUENCE CHARACTERISTICS:
         (A) LENGTH: 6
         (B) TYPE: AMINO ACID
         (C) STRANDEDNESS: Not Relevant
         (D) TOPOLOGY: CIRCULAR
```

(ii) MOLECULE TYPE:
            (A) DESCRIPTION: PEPTIDE (xi) SEQUENCE DESCRIPTION: SEQ ID NO: 13:

Xaa Thr Xaa Xaa Xaa Xaa
       1               5

(2) INFORMATION FOR SEQ ID NO: 14:

(i) SEQUENCE CHARACTERISTICS:
        (A) LENGTH: 6
        (B) TYPE: AMINO ACID
        (C) STRANDEDNESS: Not Relevant
        (D) TOPOLOGY: CIRCULAR (ii) MOLECULE TYPE:
         (A) DESCRIPTION: PEPTIDE (xi) SEQUENCE DESCRIPTION: SEQ ID NO: 14:

Xaa Thr Xaa Xaa Xaa Xaa
       1               5

(2) INFORMATION FOR SEQ ID NO: 15:

(i) SEQUENCE CHARACTERISTICS:
        (A) LENGTH: 6
        (B) TYPE: AMINO ACID
        (C) STRANDEDNESS: Not Relevant
        (D) TOPOLOGY: CIRCULAR (ii) MOLECULE TYPE:
         (A) DESCRIPTION: PEPTIDE (xi) SEQUENCE DESCRIPTION: SEQ ID NO: 15:

Xaa Thr Xaa Xaa Xaa Xaa
       1               5

(2) INFORMATION FOR SEQ ID NO: 16:

(i) SEQUENCE CHARACTERISTICS:
        (A) LENGTH: 6
        (B) TYPE: AMINO ACID
        (C) STRANDEDNESS: Not Relevant
        (D) TOPOLOGY: CIRCULAR (ii) MOLECULE TYPE:
         (A) DESCRIPTION: PEPTIDE (xi) SEQUENCE DESCRIPTION: SEQ ID NO: 16:

Xaa Ser Xaa Xaa Xaa Xaa
       1               5

(2) INFORMATION FOR SEQ ID NO: 17:

(i) SEQUENCE CHARACTERISTICS:
        (A) LENGTH: 6
        (B) TYPE: AMINO ACID
        (C) STRANDEDNESS: Not Relevant
        (D) TOPOLOGY: CIRCULAR (ii) MOLECULE TYPE:
         (A) DESCRIPTION: PEPTIDE (xi) SEQUENCE DESCRIPTION: SEQ ID NO: 17:

Xaa Thr Xaa Xaa Xaa Xaa
       1               5

(2) INFORMATION FOR SEQ ID NO: 18:

(i) SEQUENCE CHARACTERISTICS:
              (A) LENGTH: 6
              (B) TYPE: AMINO ACID
              (C) STRANDEDNESS: Not Relevant
              (D) TOPOLOGY: CIRCULAR (ii) MOLECULE TYPE:
              (A) DESCRIPTION: PEPTIDE (xi) SEQUENCE DESCRIPTION: SEQ ID NO: 18:

Xaa Thr Xaa Xaa Xaa Xaa
           1               5

(2) INFORMATION FOR SEQ ID NO: 19:

(i) SEQUENCE CHARACTERISTICS:
              (A) LENGTH: 6
              (B) TYPE: AMINO ACID
              (C) STRANDEDNESS: Not Relevant
              (D) TOPOLOGY: CIRCULAR (ii) MOLECULE TYPE:
              (A) DESCRIPTION: PEPTIDE (xi) SEQUENCE DESCRIPTION: SEQ ID NO: 19:

Xaa Thr Xaa Xaa Xaa Xaa
           1               5

(2) INFORMATION FOR SEQ ID NO: 20:

(i) SEQUENCE CHARACTERISTICS:
              (A) LENGTH: 6
              (B) TYPE: AMINO ACID
              (C) STRANDEDNESS: Not Relevant
              (D) TOPOLOGY: CIRCULAR (ii) MOLECULE TYPE:
              (A) DESCRIPTION: PEPTIDE (xi) SEQUENCE DESCRIPTION: SEQ ID NO: 20:

Xaa Thr Xaa Xaa Xaa Xaa
           1               5

(2) INFORMATION FOR SEQ ID NO: 21:

(i) SEQUENCE CHARACTERISTICS:
              (A) LENGTH: 6
              (B) TYPE: AMINO ACID
              (C) STRANDEDNESS: Not Relevant
              (D) TOPOLOGY: CIRCULAR (ii) MOLECULE TYPE:
              (A) DESCRIPTION: PEPTIDE (xi) SEQUENCE DESCRIPTION: SEQ ID NO: 21:

Xaa Thr Xaa Xaa Xaa Xaa
           1               5

(2) INFORMATION FOR SEQ ID NO: 22:

(i) SEQUENCE CHARACTERISTICS:
              (A) LENGTH: 6
              (B) TYPE: AMINO ACID
              (C) STRANDEDNESS: Not Relevant
              (D) TOPOLOGY: CIRCULAR (ii) MOLECULE TYPE:
              (A) DESCRIPTION: PEPTIDE (xi) SEQUENCE DESCRIPTION: SEQ ID NO: 22:

Xaa Thr Xaa Xaa Xaa Xaa

```
            1               5
```

(2) INFORMATION FOR SEQ ID NO: 23:

(i) SEQUENCE CHARACTERISTICS:
        (A) LENGTH: 6
        (B) TYPE: AMINO ACID
        (C) STRANDEDNESS: Not Relevant
        (D) TOPOLOGY: CIRCULAR (ii) MOLECULE TYPE:
        (A) DESCRIPTION: PEPTIDE (xi) SEQUENCE DESCRIPTION: SEQ ID NO: 23:

```
        Xaa Ser Xaa Xaa Xaa Xaa
         1               5
```

(2) INFORMATION FOR SEQ ID NO: 24:

(i) SEQUENCE CHARACTERISTICS:
        (A) LENGTH: 6
        (B) TYPE: AMINO ACID
        (C) STRANDEDNESS: Not Relevant
        (D) TOPOLOGY: CIRCULAR (ii) MOLECULE TYPE:
        (A) DESCRIPTION: PEPTIDE (xi) SEQUENCE DESCRIPTION: SEQ ID NO: 24:

```
        Xaa Ser Xaa Xaa Xaa Xaa
         1               5
```

(2) INFORMATION FOR SEQ ID NO: 25:

(i) SEQUENCE CHARACTERISTICS:
        (A) LENGTH: 6
        (B) TYPE: AMINO ACID
        (C) STRANDEDNESS: Not Relevant
        (D) TOPOLOGY: CIRCULAR (ii) MOLECULE TYPE:
        (A) DESCRIPTION: PEPTIDE (xi) SEQUENCE DESCRIPTION: SEQ ID NO: 25:

```
        Xaa Thr Xaa Xaa Xaa Xaa
         1               5
```

(2) INFORMATION FOR SEQ ID NO: 26:

(i) SEQUENCE CHARACTERISTICS:
        (A) LENGTH: 6
        (B) TYPE: AMINO ACID
        (C) STRANDEDNESS: Not Relevant
        (D) TOPOLOGY: CIRCULAR (ii) MOLECULE TYPE:
        (A) DESCRIPTION: PEPTIDE (xi) SEQUENCE DESCRIPTION: SEQ ID NO: 26:

```
        Xaa Thr Xaa Xaa Xaa Xaa
         1               5
```

(2) INFORMATION FOR SEQ ID NO: 27:

(i) SEQUENCE CHARACTERISTICS:
        (A) LENGTH: 6
        (B) TYPE: AMINO ACID
        (C) STRANDEDNESS: Not Relevant
        (D) TOPOLOGY: CIRCULAR (ii) MOLECULE TYPE:

(A) DESCRIPTION: PEPTIDE (xi) SEQUENCE DESCRIPTION: SEQ ID NO: 27:

Xaa Thr Xaa Xaa Xaa Xaa
         1               5

(2) INFORMATION FOR SEQ ID NO: 28:

(i) SEQUENCE CHARACTERISTICS:
           (A) LENGTH: 6
           (B) TYPE: AMINO ACID
           (C) STRANDEDNESS: Not Relevant
           (D) TOPOLOGY: CIRCULAR (ii) MOLECULE TYPE:
           (A) DESCRIPTION: PEPTIDE (xi) SEQUENCE DESCRIPTION: SEQ ID NO: 28:

Xaa Thr Xaa Xaa Xaa Xaa
         1               5

(2) INFORMATION FOR SEQ ID NO: 29:

(i) SEQUENCE CHARACTERISTICS:
           (A) LENGTH: 6
           (B) TYPE: AMINO ACID
           (C) STRANDEDNESS: Not Relevant
           (D) TOPOLOGY: CIRCULAR (ii) MOLECULE TYPE:
           (A) DESCRIPTION: PEPTIDE (xi) SEQUENCE DESCRIPTION: SEQ ID NO: 29:

Xaa Ser Xaa Xaa Xaa Xaa
         1               5

(2) INFORMATION FOR SEQ ID NO: 30:

(i) SEQUENCE CHARACTERISTICS:
           (A) LENGTH: 6
           (B) TYPE: AMINO ACID
           (C) STRANDEDNESS: Not Relevant
           (D) TOPOLOGY: CIRCULAR (ii) MOLECULE TYPE:
           (A) DESCRIPTION: PEPTIDE (xi) SEQUENCE DESCRIPTION: SEQ ID NO: 30:

Xaa Thr Xaa Xaa Xaa Xaa
         1               5

(2) INFORMATION FOR SEQ ID NO: 31:

(i) SEQUENCE CHARACTERISTICS:
           (A) LENGTH: 6
           (B) TYPE: AMINO ACID
           (C) STRANDEDNESS: Not Relevant
           (D) TOPOLOGY: CIRCULAR (ii) MOLECULE TYPE:
           (A) DESCRIPTION: PEPTIDE (xi) SEQUENCE DESCRIPTION: SEQ ID NO: 31:

Xaa Thr Xaa Xaa Xaa Xaa
         1               5

(2) INFORMATION FOR SEQ ID NO: 32:

(i) SEQUENCE CHARACTERISTICS:
           (A) LENGTH: 6

(B) TYPE: AMINO ACID
        (C) STRANDEDNESS: Not Relevant
        (D) TOPOLOGY: CIRCULAR (ii) MOLECULE TYPE:
        (A) DESCRIPTION: PEPTIDE (xi) SEQUENCE DESCRIPTION: SEQ ID NO: 32:

Xaa Thr Xaa Xaa Xaa Xaa
     1               5

(2) INFORMATION FOR SEQ ID NO: 33:

(i) SEQUENCE CHARACTERISTICS:
        (A) LENGTH: 6
        (B) TYPE: AMINO ACID
        (C) STRANDEDNESS: Not Relevant
        (D) TOPOLOGY: CIRCULAR (ii) MOLECULE TYPE:
        (A) DESCRIPTION: PEPTIDE (xi) SEQUENCE DESCRIPTION: SEQ ID NO: 33:

Xaa Thr Xaa Xaa Xaa Xaa
     1               5

(2) INFORMATION FOR SEQ ID NO: 34:

(i) SEQUENCE CHARACTERISTICS:
        (A) LENGTH: 6
        (B) TYPE: AMINO ACID
        (C) STRANDEDNESS: Not Relevant
        (D) TOPOLOGY: CIRCULAR (ii) MOLECULE TYPE:
        (A) DESCRIPTION: PEPTIDE (xi) SEQUENCE DESCRIPTION: SEQ ID NO: 34:

Xaa Thr Xaa Xaa Xaa Xaa
     1               5

(2) INFORMATION FOR SEQ ID NO: 35:

(i) SEQUENCE CHARACTERISTICS:
        (A) LENGTH: 6
        (B) TYPE: AMINO ACID
        (C) STRANDEDNESS: Not Relevant
        (D) TOPOLOGY: CIRCULAR (ii) MOLECULE TYPE:
        (A) DESCRIPTION: PEPTIDE (xi) SEQUENCE DESCRIPTION: SEQ ID NO: 35:

Xaa Thr Xaa Xaa Xaa Xaa
     1               5

(2) INFORMATION FOR SEQ ID NO: 36:

(i) SEQUENCE CHARACTERISTICS:
        (A) LENGTH: 6
        (B) TYPE: AMINO ACID
        (C) STRANDEDNESS: Not Relevant
        (D) TOPOLOGY: CIRCULAR (ii) MOLECULE TYPE:
        (A) DESCRIPTION: PEPTIDE (xi) SEQUENCE DESCRIPTION: SEQ ID NO: 36:

Xaa Ser Xaa Xaa Xaa Xaa
     1               5

(2) INFORMATION FOR SEQ ID NO: 37:

(i) SEQUENCE CHARACTERISTICS:
        (A) LENGTH: 6
        (B) TYPE: AMINO ACID
        (C) STRANDEDNESS: Not Relevant
        (D) TOPOLOGY: CIRCULAR (ii) MOLECULE TYPE:
        (A) DESCRIPTION: PEPTIDE (xi) SEQUENCE DESCRIPTION: SEQ ID NO: 37:

Xaa Ser Xaa Xaa Xaa Xaa
    1             5

(2) INFORMATION FOR SEQ ID NO: 38:

(i) SEQUENCE CHARACTERISTICS:
        (A) LENGTH: 6
        (B) TYPE: AMINO ACID
        (C) STRANDEDNESS: Not Relevant
        (D) TOPOLOGY: CIRCULAR (ii) MOLECULE TYPE:
        (A) DESCRIPTION: PEPTIDE (xi) SEQUENCE DESCRIPTION: SEQ ID NO: 38:

Xaa Thr Xaa Xaa Xaa Xaa
    1             5

(2) INFORMATION FOR SEQ ID NO: 39:

(i) SEQUENCE CHARACTERISTICS:
        (A) LENGTH: 6
        (B) TYPE: AMINO ACID
        (C) STRANDEDNESS: Not Relevant
        (D) TOPOLOGY: CIRCULAR (ii) MOLECULE TYPE:
        (A) DESCRIPTION: PEPTIDE (xi) SEQUENCE DESCRIPTION: SEQ ID NO: 39:

Xaa Thr Xaa Xaa Xaa Xaa
    1             5

(2) INFORMATION FOR SEQ ID NO: 40:

(i) SEQUENCE CHARACTERISTICS:
        (A) LENGTH: 6
        (B) TYPE: AMINO ACID
        (C) STRANDEDNESS: Not Relevant
        (D) TOPOLOGY: CIRCULAR (ii) MOLECULE TYPE:
        (A) DESCRIPTION: PEPTIDE (xi) SEQUENCE DESCRIPTION: SEQ ID NO: 40:

Xaa Thr Xaa Xaa Xaa Xaa
 1   5

(2) INFORMATION FOR SEQ ID NO: 41:

(i) SEQUENCE CHARACTERISTICS:
        (A) LENGTH: 6
        (B) TYPE: AMINO ACID
        (C) STRANDEDNESS: Not Relevant
        (D) TOPOLOGY: CIRCULAR (ii) MOLECULE TYPE:
        (A) DESCRIPTION: PEPTIDE

```
        (xi) SEQUENCE DESCRIPTION: SEQ ID NO: 41:

Xaa Thr Xaa Xaa Xaa Xaa
 1               5

(2) INFORMATION FOR SEQ ID NO: 42:

(i) SEQUENCE CHARACTERISTICS:
        (A) LENGTH: 6
        (B) TYPE: AMINO ACID
        (C) STRANDEDNESS: Not Relevant
        (D) TOPOLOGY: CIRCULAR (ii) MOLECULE TYPE:
        (A) DESCRIPTION: PEPTIDE (xi) SEQUENCE DESCRIPTION: SEQ ID NO: 42:

Xaa Thr Xaa Xaa Xaa Xaa
 1               5
```

CYCLOHEXAPEPTIDYL PROPANOLAMINE COMPOUNDS

This application is a continuation-in-part of application Ser. No. 07/771,017, filed Oct. 1, 1991, abandoned.

The present invention is directed to certain cyclohexapeptidyl propanolamine compounds and to a process for their preparation.

The cyclohexapeptidyl propanolamine compounds of the present invention, Compound A (SEQ ID NOS 1–13 and 40, 41) may be represented by (A) an amine, Compound A-I (SEQ ID NOS 1–13, 40 and 41), represented by the formula:

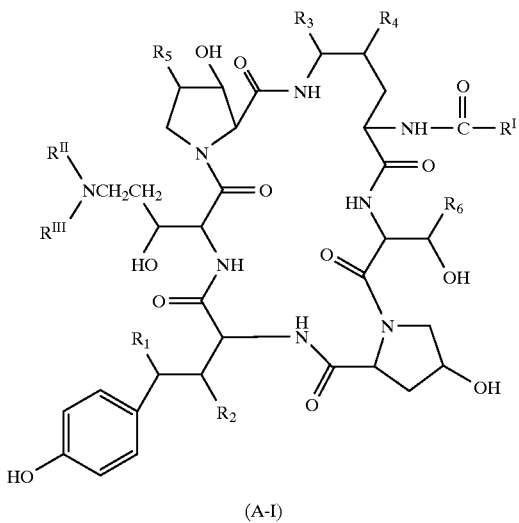

(A-I)

or its acid addition salt, or (B) a quaternary ammonium salt, Compound A-II (SEQ ID NOS 1–13, 40 and 41), represented by the formula

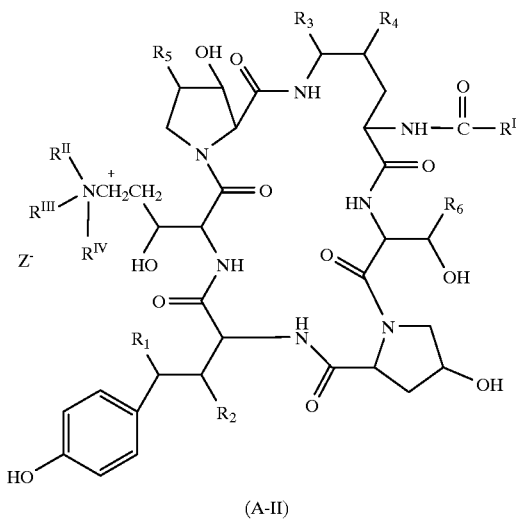

(A-II)

In the foregoing and succeeding formulas, $R_1$ is H or OH $R_2$ is H or OH $R_3$ is H, OH or OR where R is $C_1$–$C_4$ alkyl or benzyl $R_4$ is H or OH $R_5$ is H, OH or $CH_3$ $R_6$ is H or $CH_3$ $R^I$ is $C_9$–$C_{21}$ alkyl, $C_9$–$C_{21}$ alkenyl, $C_1$–$C_{10}$ alkoxyphenyl, or $C_1$–$C_{10}$ alkoxynaphthyl;

$R^{II}$ is H, $C_1$–$C_4$ alkyl or benzyl, $R^{III}$ is H, $C_1$–$C_4$ alkyl or benzyl or $R^{II}$ and $R^{III}$ together is —$(CH_2)_4$—6;

$R^{IV}$ is H or $C_1$–$C_4$ alkyl; and

Z is an anion of a pharmaceutically acceptable salt.

Hereinafter, when the expression "cyclohexapeptidyl propanolamine compound" or "Compound A" is employed, it is intended to embrace the propanolamine of formula (A-I), its acid addition salt and quaternary ammonium salt of formula (A-II). "Compound A-I" will refer to the acid addition salt as well as the free base.

Where the expression "alkyl", "alkenyl", or "alkoxy" is employed, it is intended to include branched as well as straight chain radicals.

Pharmaceutically acceptable salts suitable as acid addition salts as well as salts providing the anion of the quaternary salt are those from acids such as hydrochloric, hydrobromic, phosphoric, sulfuric, maleic, citric, acetic, tartaric, succinic, oxalic, malic, glutamic and the like, and include other acids related to the pharmaceutically acceptable salts listed in Journal of Pharmaceutical Science, 66, 2 (1977).

Representative nuclei for the propanolamine compounds, Compound A, and the sequence ID for these compounds may be seen in the following table. Since the amino acid nuclei would be the same irrespective of substituents $R^I$, $R^{II}$, $R^{III}$, or $R^{IV}$ the sequence identification number is assigned for the nuclear variations so that the amines and ammonium salts have the same sequence ID's, as well as compounds having a different lipophilic side chain.

| AMINE COMPOUND | $R_1$ | $R_2$ | $R_3$ | $R_4$ | $R_5$ | $R_6$ | SEQ. ID |
|---|---|---|---|---|---|---|---|
| A-1 | OH | OH | OH | OH | H | $CH_3$ | 1 |
| A-2 | OH | OH | OH | OH | $CH_3$ | $CH_3$ | 2 |
| A-3 | H | OH | OH | OH | $CH_3$ | H | 3 |
| A-4 | OH | H | OH | OH | $CH_3$ | $CH_3$ | 4 |
| A-5 | H | H | OH | H | $CH_3$ | $CH_3$ | 5 |
| A-6 | H | H | H | H | $CH_3$ | $CH_3$ | 6 |
| A-7 | OH | OH | H | H | $CH_3$ | $CH_3$ | 7 |
| A-8 | OH | OH | H | H | H | $CH_3$ | 8 |
| A-9 | OH | OH | OH | OH | OH | $CH_3$ | 9 |
| A-10 | H | OH | OH | OH | H | H | 10 |
| A-11 | H | OH | $OCH_3$ | OH | $CH_3$ | H | 11 |
| A-12 | H | OH | H | OH | H | $CH_3$ | 12 |
| A-13 | OH | OH | H | OH | H | $CH_3$ | 13 |
| A-14 | H | OH | OH | OH | H | $CH_3$ | 40 |
| A-15 | OH | OH | $OCH_3$ | OH | H | $CH_3$ | 41 |

Compounds which are particularly outstanding for the control of mycotic infections are, Compound A-I-1a (Seq. ID No. 1) and A-I-12a (Seq. ID No. 12) represented by the following formulas:

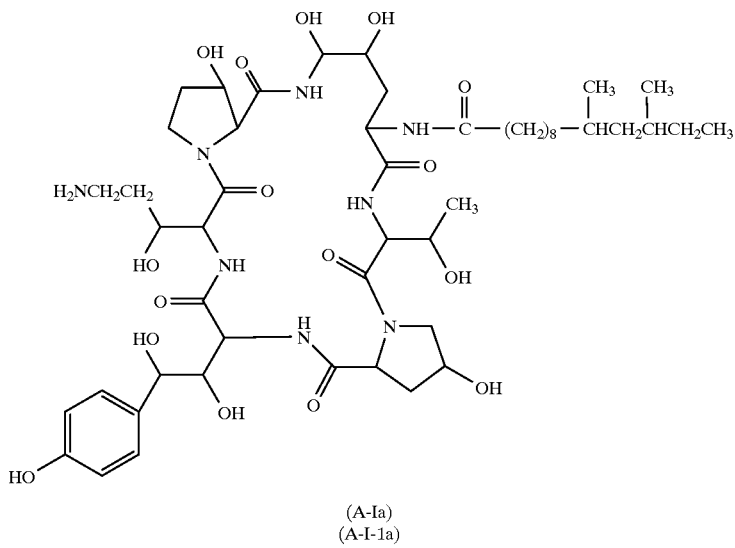

(A-Ia)
(A-I-1a)

(In the above designation "A-I" refers to the amine rather than the quaternary ammonium salt, "1" refers to compounds having nuclear substituents $R_1$ through $R_6$ which corresponds to Seq. ID No. 1, and "a" refers to the first specific compound of such designation being named in the same nuclear series. The first compound of the quaternary ammonium salt and Seq. ID No. 1 would be "A-II-1a".)

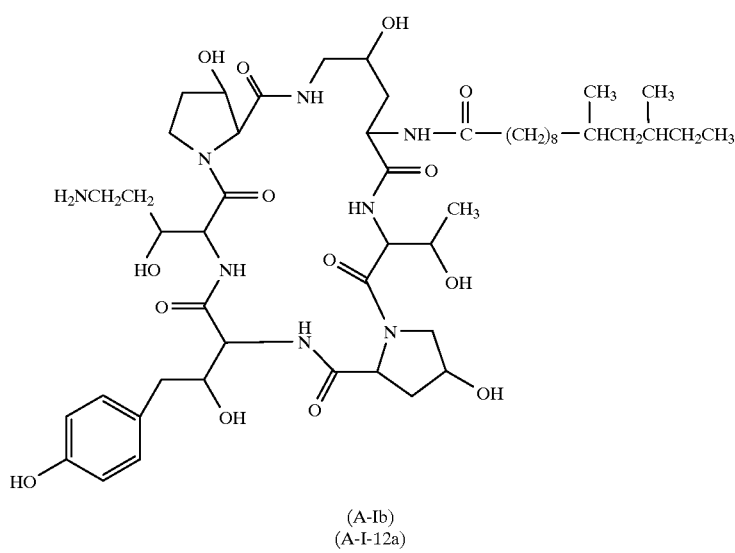

(A-Ib)
(A-I-12a)

When the compound is a free amine, they are soluble in lower alcohols and polar aprotic solvents such as dimethylformamide (DMF) and pyridine. They are insoluble in solvents such as ether and acetonitrile. The compounds in which $R_3$ is OH may be slowly degraded in aqueous media so they are preferably utilized as acid addition salts.

The compounds of the present invention are useful as an antibiotic, especially as an antifungal agent or as an antiprotozoal agent. As antifungal agents they are useful for the control of both filamentous fungi and yeasts. They are especially adaptable to be employed for the treatment of mycotic infections in mammals, especially those caused by Candida species such as *C. albicans, C. tropicalis* and *C. pseudotropicalis* and Asperigillus species such as *A. fumigatas, A. flavus, A. niger*. They are also useful for the treatment and/or prevention of *Pneumocystis carinii* pneumonia to which immune compromised patients are especially susceptible as hereinafter described.

The previously noted solubility properties are advantageous for utilization in therapeutic applications, especially in injectible compositions.

The compounds of the present invention which are amines, Compounds A-I (Seq. ID Nos. 1–13, 40 and 41) may be prepared from a nitrile which in turn is obtained from a natural product or a derivative of a natural product.

The nitrites may be represented by compounds of formula (F) (Seq. ID Nos. 14–26 and 42) and the starting materials may be represented by compound formula (E) (Seq. ID Nos. 27–39) as seen in the following diagram:

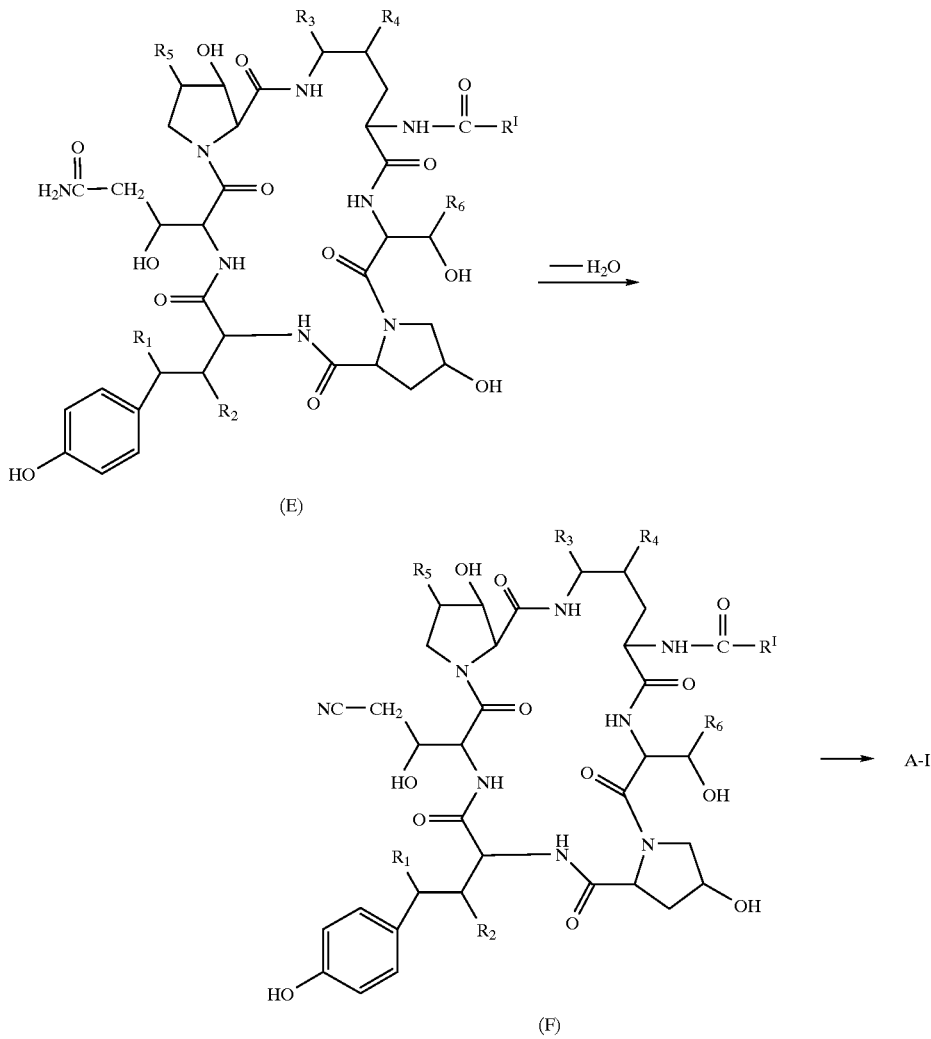

When the quaternary ammonium salt is desired, Compound A-I (Seq. ID Nos. 1–13, 40 and 41) may be quaternized using conventional procedures.

The nitriles (Compound F) are novel and useful compounds in addition to being useful intermediates in the preparation of the amines (Compound A) and are claimed in a simultaneously filed copending application, 07/936,434, now U.S. Pat. No. 5,348,940 which is a continuation-in-part of Ser. No. 07/771,017, filed Oct. 1, 1991. The starting materials for the nitriles are natural products or derivatives of natural products and are from various sources and may be obtained as subsequently described.

The sequence identification for the Compound F (Seq. ID Nos. 14–26 and 42) nitriles which correspond to the novel amines are seen below.

| NITRILE COMPOUND | $R_1$ | $R_2$ | $R_3$ | $R_4$ | $R_5$ | $R_6$ | Seq. ID |
|---|---|---|---|---|---|---|---|
| F-1 | OH | OH | OH | OH | H | $CH_3$ | 14 |
| F-2 | OH | OH | OH | OH | $CH_3$ | $CH_3$ | 15 |
| F-3 | H | OH | OH | OH | $CH_3$ | H | 16 |
| F-4 | OH | H | OH | OH | $CH_3$ | $CH_3$ | 17 |
| F-5 | H | H | OH | H | $CH_3$ | $CH_3$ | 18 |
| F-6 | H | H | H | H | $CH_3$ | $CH_3$ | 19 |
| F-7 | OH | OH | H | H | $CH_3$ | $CH_3$ | 20 |
| F-8 | OH | OH | H | H | H | $CH_3$ | 21 |
| F-9 | OH | OH | OH | OH | OH | $CH_3$ | 22 |
| F-10 | H | OH | OH | OH | H | H | 23 |
| F-11 | H | OH | $OCH_3$ | OH | $CH_3$ | H | 24 |
| F-12 | H | OH | H | OH | H | $CH_3$ | 25 |
| F-13 | OH | OH | H | OH | H | $CH_3$ | 26 |
| F-14 | H | OH | OH | OH | H | $CH_3$ | 42 |

The sequence identification numbers for the starting materials, Compound E (Seq. ID Nos. 27–39), which correspond to the nitriles and ultimately the amines are seen below,

| STARTING MATERIAL | $R_1$ | $R_2$ | $R_3$ | $R_4$ | $R_5$ | $R_6$ | Seq. ID |
|---|---|---|---|---|---|---|---|
| E-1 | OH | OH | OH | OH | H | $CH_3$ | 27 |
| E-2 | OH | OH | OH | OH | $CH_3$ | $CH_3$ | 28 |
| E-3 | H | OH | OH | OH | $CH_3$ | H | 29 |
| E-4 | OH | H | OH | OH | $CH_3$ | $CH_3$ | 30 |
| E-5 | H | H | OH | H | $CH_3$ | $CH_3$ | 31 |
| E-6 | H | H | H | H | $CH_3$ | $CH_3$ | 32 |
| E-7 | OH | OH | H | H | $CH_3$ | $CH_3$ | 33 |
| E-8 | OH | OH | H | H | H | $CH_3$ | 34 |
| E-9 | OH | OH | OH | OH | OH | $CH_3$ | 35 |
| E-10 | H | OH | OH | OH | H | H | 36 |
| E-11 | H | OH | $OCH_3$ | OH | $CH_3$ | H | 37 |
| E-12 | H | OH | H | OH | H | $CH_3$ | 38 |
| E-13 | OH | OH | H | OH | H | $CH_3$ | 39 |

In the preparation of Compound A-I (Seq. ID Nos. 1–13) the carboxamide group of Compound E is dehydrated to the nitrile Compound F. When this method is employed the reaction is preferably carried out under nitrogen with cyanuric chloride in a solvent. It may be carried out in the presence of molecular sieves but if carried out in the absence of sieves, reaction time is critical, and usually order of addition becomes important. In the absence of sieves, or without careful control of reaction time, degradation may occur even when the $R_3$ hydroxyl is protected with an ether group.

Suitable reagents which may be employed in place of cyanuric chloride are anhydrides such as acetic anhydride, trifluoroacetic anhydride and phosphorus pentoxide; acid chlorides such as oxalyl chloride, phosphorus oxychloride, thionyl chloride, p-toluenesulfonyl chloride and chlorosulfonyl isocyanate; phosphonium reagents such as phosphorus pentachloride, triphenylphosphine/carbon tetrachloride, triphenylphosphonium ditriflate and triphenylphosphonium dichloride; carbodiimides such as dicyclohexylcarbodiimide; other dehydrating agents such as aluminum chloride, titanium tetrachloride, ethyl(carboxysulfamoyl) triethylammonium hydroxide and inner salt.

Suitable solvents include dimethylformamide or weakly basic solvents such as pyridine, collidine and the like.

Molecular sieves may be in the size range 3A to 5A.

The relative amounts of Compound E (Seq. ID Nos. 27–39) and reagents vary, but in general the dehydrating agent is used in excess. From about 1.5 to 15 equivalents of the dehydrating agent are employed. The molecular sieves are used in amounts of 1 to 10 equivalents.

In carrying out the reaction using sieves, a suspension of molecular sieves in a rigorously dried solvent is first prepared, and while stirring under an atmosphere of nitrogen, there is added, cyanuric chloride or other dehydrating agent and thoroughly mixed. To the resulting mixture while stirring under an atmosphere of nitrogen is added the starting material, Compound E and the stirring continued for about 12 to 24 hours or until HPLC analysis of the reaction mixture indicates substantial completion of the reaction with the formation of the nitrile. The sieves are removed by filtration, preferably on a sintered glass funnel, and the filtrate concentrated and purified by preparative HPLC. The mobile phase used in the purification are varying ratios of a water/acetonitrile composition and an acetonitrile/water composition. These compositions are referred to in the examples as A and B. Composition A is 95/5 water/acetonitrile containing 0.1% trifluoroacetic acid (TFA) or acetic acid. Composition B is 95/5 acetonitrile/water containing 0.1% TFA or acetic acid. The exact mobile phase used for HPLC assays and the mobile phase used in preparative HPLCs may differ not only from each other but also from compound to compound but can be determined by the skilled artisan without difficulty.

In carrying out the reaction in the absence of sieves, solid cyanuric chloride is added in a single portion to a solution of Compound E in an aprotic solvent and stirred rapidly for a short time and the reaction mixture then quenched by adding aqueous sodium acetate directly to the reaction mixture. The volatiles are then removed in vacuo to obtain a solid residue which may be purified as above described.

The reduction of the nitrile to the amine may be carried out employing either chemical or catalytic reduction. Sodium borohydride with cobaltous chloride in alcoholic solvent has been found to be particularly useful. When this combination of reagents is used, from about 5 to 50 molar equivalent of sodium borohydride and from 2 to 10 molar equivalents of cobaltous chloride are used for each molar amount of the nitrile.

Other hydride reducing agents such as sodium borohydride, aluminum hydride, diborane, diisobutyl aluminum hydride and the like also may be used. Frequently these reducing agents are used in combination with a Lewis acid such as cobaltous chloride or aluminum chloride as in the present combination of sodium borohydride and cobaltous chloride.

Catalytic hydrogenation also may be carried out over a variety of catalysts including palladium on carbon, platinum oxide, or rhodium on alumina.

Typical solvents depending on the reagent include alcohols, especially methanol and ethanol, dimethylformamide, pyridine, tetrahydrofuran or other ethers.

When the reduction of the nitrile to the amine is carried out using the preferred chemical procedure, the reaction may be carried out by adding the chemical reducing agent to the nitrile in an alcoholic solution under an atmosphere of nitrogen, and stirring until HPLC analysis using detection by ultraviolet absorption at 210 nm shows substantial completion of the reaction. When sodium borohydride is used in combination with cobaltous chloride, cobaltous chloride is added while stirring to a solution in methanol or other solvent of the nitrile, prepared as above described, at ambient temperature, followed by portionwise addition of the sodium borohydride which is accompanied by gas evolution. Stirring is continued for from 12 to 24 hours. Then the mixture is diluted with a highly aqueous mobile phase, 70/30 to 50/50 A:B, acidified with acetic acid or hydrochloric acid conveniently as indicated by pH paper,filtered and purified by chromatography. The eluate fractions are lyophilized to obtain the amine as an acetic acid addition salt.

The N-alkylated or benzylated compounds may be prepared using any suitable known procedure for preparing secondary or tertiary amines. The N-benzyl compound is best prepared by first preparing a Schiff base with benzaldehyde and thereafter reducing with conventional reducing agents such as those previously noted in connection with the reduction of the nitrile although milder reducing agents may be employed.

When the desired alkyl group on the nitrogen is methyl, the carbon may be introduced by formylating, followed by reduction of the hydroxymethyl group with sodium cyanoborohydride or other reducing agent. When the desired alkyl group on the nitrogen is a higher alkyl, a preferred procedure is a reductive alkylation of an N-benzyl derivative with an aldehyde and a reducing agent such as cyanoborohydride, and purifying the product with reverse phase chromatography to obtain a benzyl and a higher alkyl substituted tertiary amine. The benzyl group may be removed by hydrogenation using palladium on carbon or other suitable catalyst.

When the alkyl groups are the same, the same general procedure is preferably employed. Although alkyl halide or sulfate may be employed, these are best for quaternary salts.

When the ultimate product is a quaternary ammonium salt, the appropriate amine prepared as above described is caused to react with an alkylating agent such as alkyl iodide, other alkyl halide, or alkyl sulfate in the presence of sodium bicarbonate in an inert solvent. A slight molar excess of sodium bicarbonate is employed. The alkylating agent is used in large molar excess. About six to tenfold molar excess may be employed.

When all substituents on the nitrogen are the same, the starting amine may be the primary amine. For mixed amines, it is preferable to enter the specific groups first since alkylation using an alkylating agent is more difficult to control.

The compounds in which $R_3$ is an ether group may be prepared by reacting the cyclopeptide amine compound or the starting material with excess alcohol in the presence of an acid such as camphorsulfonic acid and thereafter recovering by preparative HPLC using acetonitrile/water as the mobile phase.

The compounds of the present invention are active against many fungi and particularly against Candida species. The antifungal properties may be illustrated with the minimum fungicidal concentration (MFC) determination against certain Candida and Cryptococcus organisms in a microbroth dilution assay carried out in a Yeast Nitrogen Base (Difco) medium with 1% dextrose (YNBD).

In a representative assay, Compound A-Ia was solubilized in 100% dimethyl sulfoxide (DMSO) at an initial concentration of 5 mg/ml. Once dissolved, the drug stock was brought to a concentration of 512 $\mu$g/ml by dilution in water such that the final DMSO concentration was about 10 percent. The solution was then dispensed via a multichannel pipette into the first column of a 96-well plate (each well containing 0.075 ml of YNBD), resulting in a drug concentration of 256 $\mu$g/ml. Compounds in the first column were diluted 2-fold across the rows yielding final drug concentrations ranging from 256 $\mu$g/ml to 0.12 $\mu$g/ml.

Four-hour broth cultures of organisms to be tested were adjusted using a spectrophotometer at 600 nm to equal a 0.5 McFarland Standard. This suspension was diluted 1:100 in YNBD to yield a cell concentration of 1-5×10$^4$ colony forming units (CFU)/ml. Aliquots of the suspension (0.075 ml) were inoculated into each well of the microtiter plate resulting in a final cell inoculum of 5-25 ×10$^3$. CFU/ml and final drug concentrations ranging from 128 $\mu$g/ml to 0.06 $\mu$g/ml. Each assay includes one row for drug-free control wells and one row for cell-free control wells.

After 24 hours of incubation, the microtiter plates were shaken gently on a shaker to resuspend the cells. The MIC-2000 inoculator was used to transfer a 1.5 microtiter sample from each well of the 96-well microtiter plate to a single reservoir inoculum plate containing Sabouraud dextrose agar (SDA). The inoculated SDA plates were incubated for 24 hours at 35° C. However, for Cryptoccoccus neoformans strains, SDA plates were inoculated at 48 hours and incubated 48 hours after being spotted on SDA before making miniumum fungicidal concentration (MFC) readings. The results were as follows:

| Organism | | MFC $\mu$g/mL |
|---|---|---|
| C. albicans | MY 1028 | <0.06 |
| C. albicans | MY 1055 | 0.12 |
| C. albicans | MY 1750 | 0.12 |
| L. guillermondii | NY 1019 | 0.5 |
| C. parapsilosis | MY 1010 | 0.5 |
| C. pseudotropicalis | MY 2099 | <0.06 |
| C. tropicalis | MY 1012 | <0.06 |
| Cr. neoformans | MY 1051 | 16 |
| Cr. neoformans | MY 1146 | 32 |
| Cr. neoformans | MY 2061 | 32 |
| Cr. neoformans | MY 2062 | 16 |

The compounds also show in vivo effectiveness against fungi which may be demonstrated with Compound A-I-1a.

Growth from an overnight SDA culture of Candida albicans MY 1055 was suspended in sterile saline and the cell concentration determined by hemacytometer count and the cell suspension adjusted to 3.75×10$^5$ cells/ml. Then 0.2 milliliter of this suspension was administered I.V. in the tail vein of mice so that the final inoculum was 7.5×10$^4$ cells/mouse.

The assay then was carried out by administering aqueous solutions of Compound A-I-1a at various concentrations intraperitoneally (I.P.), twice daily (b.i.d.) for four consecutive days to 18 to 20 gram female DBA/2 mice, which previously had been infected with Candida albicans in the manner described above. Distilled water was administered I.P. to C. albicans challenged mice as controls. After seven days, the mice were sacrificed by carbon dioxide gas, paired kidneys were removed aseptically and placed in sterile polyethylene bags containing 5 milliters of sterile saline. The kidneys were homogenized in the bags, serially diluted in sterile saline and aliquots spread on the surface of SDA plates. The plates were incubated at 35° C. for 48 hours and yeast colonies were enumerated for determination of colony forming units (CFU) per gram of kidneys. Compound A-I-1a gave >99 percent reduction of recoverable Candida CFUs at 6 and 1.5 mg/kg I.P. twice daily for four consecutive days.

The compounds of the present invention are also useful for inhibiting or alleviating Pneumocystis carinii infections in immune compromised patients. The efficacy of the compounds of the present invention for therapeutic or anti-infective purposes may be demonstrated in studies on immunosuppressed rats.

In a representative study, the effectiveness of Compound A-I-1a was determined. Sprague-Dawley rats (weighing approximately 250 grams) were immunosuppressed with dexasone in the drinking water (2.0 mg/L) and maintained on a low protein diet for seven weeks to induce the development of pneumocystis pneumonia from a latent infection. Before drug treatment, two rats were sacrificed to confirm the presence of Pneumocystis carinii pneumonia (PCP); both rats were found to have infections. Five rats (weighing approximately 150 grams) were injected twice daily for four days subcutaneously (sc) with Compound A-Ia in 0.25 ml of vehicle (distilled water). A vehicle control was also carried out. All animals continued to receive dexasone in the drinking water and low protein diet during the treatment period. At the completion of the treatment, all animals were sacrificed, the lungs were removed and processed, and the extent of disease determined by microscopic analysis of stained slides. The results of this study showed Compound A-I-1a was 99 percent effective in reducing P. carinii cysts in 5 rats when dosed at 0.300 mg/kg with all rats surviving.

The outstanding properties are most effectively utilized when the compound is formulated into novel pharmaceutical compositions with a pharmaceutically acceptable carrier according to conventional pharmaceutical compounding techniques.

The novel compositions contain at least a therapeutic antifungal or antipneumocystis amount of the active compound. Generally, the composition contains at least 1% by weight of Compound A or one of the components. Concentrate compositions suitable for dilutions prior to use may contain 90% or more by weight. The compositions include compositions suitable for oral, topical, parenteral (including intraperitoneal, subcutaneous, intramuscular, and intravenous), nasal, and suppository administration, or insufflation. The compositions may be prepacked by intimately mixing Compound A with the components suitable for the medium desired.

Compositions formulated for oral administration may be a liquid composition or a solid composition. For liquid preparations, the therapeutic agent may be formulated with liquid carriers such as water, glycols, oils, alcohols, and the like, and for solid preparations such as capsules and tablets, with solid carriers such as starches, sugars, kaolin, ethyl cellulose, calcium and sodium carbonate, calcium phosphate, kaolin, talc, lactose, generally with lubricant such as calcium stearate, together with binders disintegrating agents and the like. Because of their ease in administration, tablets and capsules represent the most advantageous oral dosage form. It is especially advantageous to formulate the compositions in unit dosage form (as hereinafter defined) for ease of administration and uniformity of dosage. Compositions in unit dosage form constitute an aspect of the present invention.

Compositions may be formulated for injection and for injecton take such forms as suspensions, solutions or emulsions in oily or aqueous vehicles such as 0.85 percent sodium chloride or 5 percent dextrose in water and may contain formulating agents such as suspending, stabilizing and/or dispersing agents. Buffering agents as well as additives such as saline or glucose may be added to make the solutions isotonic. The compound also may be solubilized in alcohol/propylene glycol or polyethylene glycol for drip intravenous administration. These compositions also may be presented in unit dosage form in ampoules or in multidose containers, preferably with added preservative. Alternatively, the active ingredients may be in powder form for reconstituting with a suitable vehicle prior to administration.

The term "unit dosage form" as used in the specification and claims refer to physically discrete units, each unit containing a predetermined quantity of active ingredient calculated to produce the desired therapeutic effect in association with the pharmaceutical carrier. Examples of such unit dosage forms are tablets, capsules, pills, powder packets, wafers, measured units in ampoules or in multidose containers and the like. A unit dosage of the present invention will generally contain from 100 to 200 milligrams of one of the compounds.

When the compound is for antifungal use any method of administration may be employed. For treating mycotic infections, oral administration is frequently preferred.

When the compound is to be employed for control of pneumocystis infections it is desirable to directly treat lung and bronchi. For this reason inhalation methods are preferred. For administration by inhalation, the compounds of the present invention are conveniently delivered in the form of an aerosol spray presentation from pressurized packs or nebulisers. The preferred delivery system for inhalation is a metered dose inhalation (MDI) aerosol, which may be formulated as a suspension or solution of Compound AI or A II in suitable propellants, such as fluorocarbons or hydrocarbons.

Although the compounds of the present invention may be employed as tablets, capsules, topical compositions, insufflation powders, suppositories and the like, the solubility of the compounds of the present invention in water and aqueous media render them adaptable for use in injectible formulations and also in liquid compositions suitable for aerosol sprays.

The following examples illustrate the invention but are not to be construed as limiting.

EXAMPLE I

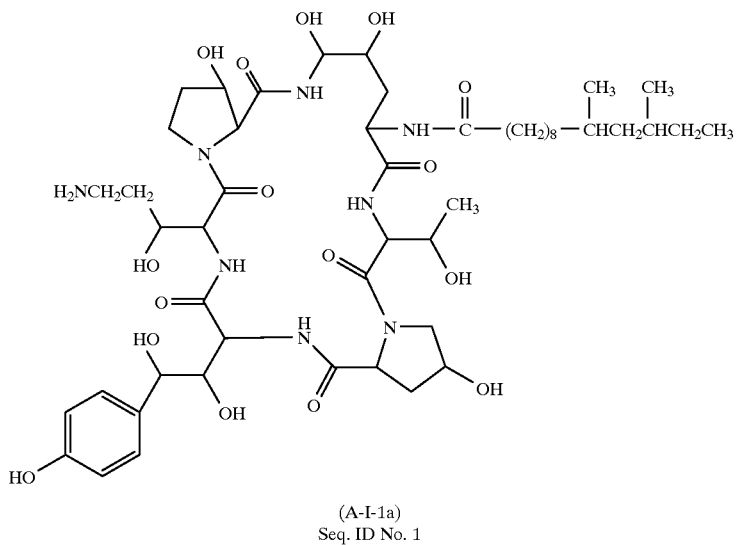

(A-I-1a)
Seq. ID No. 1

A. Preparation of Intermediate Nitrile Compound 550 milligrams (2.98 mmol; 1.5 molar eq) of cyanuric chloride was added to a suspension of 4A molecular sieves pre-prepared by stirring together 10.2 grams of 4A molecular sieves under nitrogen for 0.5 hour with 45 milliliters of DMF (predried over a combination of 13× and 3A molecular sieves), and the stirring continued for 5 minutes. To the resulting suspension was added 2.08 grams (1.95 mmol) of Compound E-1 (Seq. ID No. 27) ($R_1$, $R_2$, $R_3$ and $R_4$ are OH; $R_5$ is H; $R_6$ is $CH_3$; $R^I$ is 9,11-dimethyltridecyl). The resulting mixture still under nitrogen was then stirred for 18 hours. At the end of this period an HPLC analysis was carried out employing a "ZORBAX" (Dupont, 4.9 mm×25 cm) C8 column and eluting isocratically with 60/40 A:B (containing 0.1% TFA) at ambient temperature with detection by ultraviolet absorption at 210 nm which showed about a 2:1 ratio of product to starting material. The molecular sieves were filtered onto a sintered glass funnel and washed consecutively with 5 milliliters of DMF and 5 milliliters of methanol. The filtrate was concentrated in vacuo to a final volume of 20 milliters and filtered through a 0.45µ Whatman polypropylene syringe filter. The filtrate was diluted with mobile phase 65/35 A:B to a volume of 40 milliliters and pump injected at 10 milliliters per minute onto a Waters 45 mm ID radial compression column packed with 15µ, 100 Angstrom Δ-Pak C18 stationary phase. The column was eluted initially at 20 mL/min and the elution continued until the front running impurities had been eluted. The composition of the eluting agent was then stepped up to 60/40 A:B and the flow increased to 40 mL/min. Fractions containing the desired product were pooled and concentrated in vacuo to remove most of the acetonitrile. The residue was lyophilized to obtain 800 milligrams (40 percent yield) of the nitrile intermediate (Seq. ID No. 14). The compound had the following spectral characteristics.

$^1$H-NMR (400 MHz, $CD_3OD$): δ7.12 (d, 2H), 6.73 (d, 2H), 5.31 (d, 1H), 1.20 (d, 3H), 0.88 (t, 3H), 0.87 (d, 6H); Mass spectrum (FAB): 1054 (M+Li)

the reaction medium to black which was accompanied by gas evolution. Gas evolution accompanied each of the additions. Stirring was continued for an additional 1.5 hours. An HPLC analysis carried out at this time using a "ZORBAX" column (4.9 mm×25cm C8) and eluting isocratically at 1.5 mL/min with 45/55 A:B [composition containing 0.1% TFA] with temperature at 40° C. and reading at λ=210 nm.210 nm. The analysis showed the ratio of amine:nitrile to be ~4:1. After 24 hours, the ratio remaining the same, the reaction mixture was diluted first with 2.0 milliliters of mobile phase, 70/30 A:B, [compositions containing 0.1% acetic acid], then with acetic acid to a pH of about 5 by pH paper. The reaction mixture was then filtered through 0.45µ Whatman polypropylene syringe filter and the filter washed with methanol to a final volume of 10 mL. The solution was then injected into a Waters 25 mm×10 cm radial compression column packed 15µ, 100 Angstrom Delta-Pak $C_{18}$ stationary phase and eluted at 4.0 mL/min. The pure fractions were pooled and lyophilized to obtain 110 milligrams of Compound A-I-1a (Seq. ID No. 1) as the acetic acid addition salt, a yield of 52 percent. HPLC analysis carried out on "ZORBAX" 4.9 mm×25 cm C8 column with isocratic elution at 1.5 mL/min with 45/55 A:B [compositions containing 0.1% TFA] at a temperature of 40° C. and λ=210 nm showed the product to be of 94.6 percent purity.

$^1$H-NMR (400 MHz, $CD_3OD$): δ7.12 (d, 2H), 6.75 (d, 2H), 5.18 (d, 1H), 4.97 (d, 1H), 1.19 (d, 3H), 0.89 (t, 3H), 0.86 (d, 6H), Mass spectrum (FAB): 1058 (M+Li)

EXAMPLE II

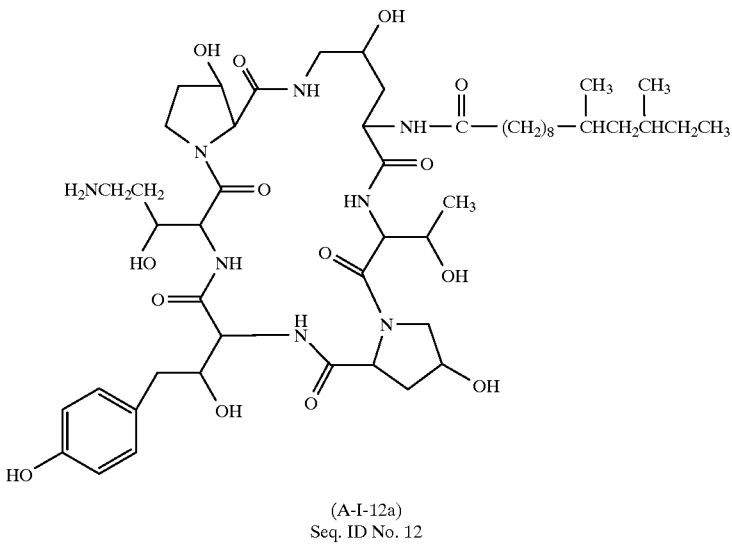

(A-I-12a)
Seq. ID No. 12

B. Preparation of Compound A-I-1a

To a solution of 210 milligrams (0.2 mmol) of the nitrile above prepared in 6.0 milliliters of methanol was added under nitrogen atmosphere, 104 milligrams (0.8 mmol, 4.0 molar eq.) of cobaltous chloride hexahydrate whereupon a purple solution formed. While the solution was stirred at room temperature, 151 milligrams (4.0 mmol, 20 molar eq) of sodium borohydride was added in four portions. The addition of sodium borohydride produced a color change in A. Preparation of Intermediate Nitrile Compound In an operation carried out in a manner similar to that described in Example I, 290 milligrams (1.57 mmol) of cyanuric chloride was added to a solution of 2.0 grams (1.94 mmol) of Compound E-12 (Seq. ID No. 38) ($R_1$ and $R_3$=H; $R_2$ and $R_4$=OH) in 8.0 milliters of DMF and the reaction mixture stirred under nitrogen for 24 hours. At this time, an additional 290 milligrams (1.57 mmol) was added and the reaction continued for one hour whereupon the reaction was judged complete by HPLC "ZORBAX" column isocratic elution with 45/55 A/B (containing 0.1% TFA) at 40° C., detection at λ=210 μm. The reaction mixture was diluted with mobile phase (50/50 A:B) and filtered through a 0.45μ Whatman polypropylene syringe filter and injected onto a Waters 45 mm I.D. radial compression column packed with 15μ, 100 A Delta-Pak C18 stationary phase. The desired fractions were combined and lyophilized to obtain 670 milligrams (34 percent) of nitrile, (Seq. ID No. 25) having a HPLC retention time of 8.0 min on a "ZORBAX" column when eluted isocratically with 45/55 A:B (containing 0.1% TFA) at 1.5 mL/min at 40° C.; detection at λ=210 nm.

$^1$H-NMR (400 MHz, CD$_3$OD): δ7.00 (d, 2H), 6.70 (d, 2H), 5.02 (d, 1H), 4.98 (d, 1H), 1.20 (d, 3H), 0.89 (t, 3H), 0.86 (d, 6H); Mass spectrum (FAB): 1020 (M+Li)

B. Preparation of Compound A-I-12a

To a solution of 60 milligrams (59 μmol) of the nitrile above prepared in 2.0 mL of methanol was added 15 milligrams (0.12 mmol) of cobaltous chloride hexahydrate followed by 22 milligrams (0.59 mmol) of sodium borohydride in three portions and the mixture stirred for about 48 hours. At this time HPLC analysis ("ZORBAX" column, isocratic elution with 45/55 A/B at 1.5 ml/min at 40° C., detection at λ=210 nm) indicated 50 percent completion. An additional portion (15 mg., 0.12 mmol) of cobaltous chloride hexahydrate was added followed by 22 milligrams (590 μmol) of sodium borohydride which was added in three portions and the resulting mixture was stirred for 72 hours. After HPLC analysis showed 70 percent completion, a final portion of 30 mg (236 μmol) of cobaltous chloride hexahydrate followed by 44 milligrams (1180 μmol in three portions) of sodium borohydride was added and the mixture stirred for 72 hours. At this time the mixture was diluted with 2.0 milliliters mobile phase of 50/50 A:B which contained 0.1 percent acetic acid instead of TFA, and then was followed with acetic acid to a pH of about 5 as determined with pH paper. The resulting mixture was then filtered through a 0.2 micron Anotop syringe filter and injected onto a Waters 25 μm×10 cm radial compression column packed with 15μ, 100 Angstrom A-Pak C18 stationary phase and eluted at 9.0 mL/min. with 50/50 A:B. The fractions were pooled and lyophilized to obtain 22 milligrams (33 percent yield) of product, Compound A-I-12a (Seq. ID No. 12) as acetic acid salt of 95.6 percent purity as determined by HPLC.

$^1$H-NMR (400 MHz, CD$_3$OD): δ6.99 (d, 2H), 6.70 (d, 2H), 4.98 (d, 1H), 1.19 (d, 3H), 0.88 (t, 3H), 0.86 (d, 6H) Mass spectrum (FAB): 1019 (M+H)

EXAMPLE III

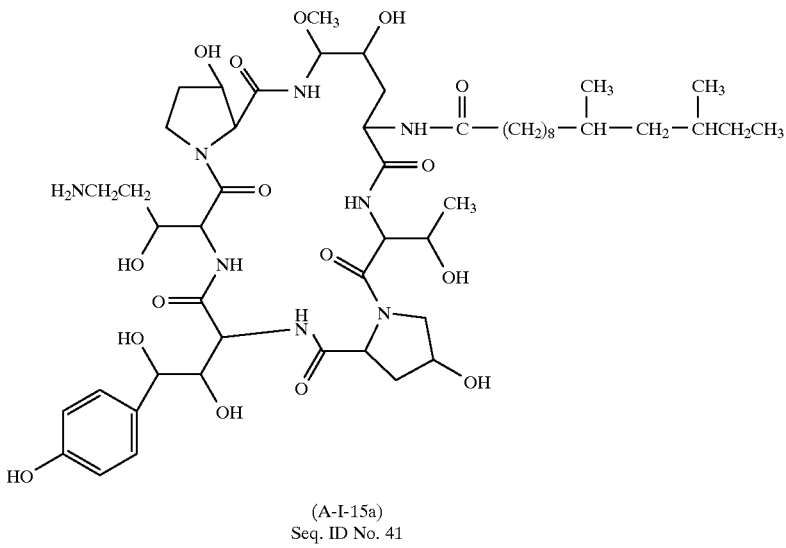

(A-I-15a)
Seq. ID No. 41

To a solution of 44 milligrams (42 μmol) of Compound A-I-1a (Seq. ID No. 1) (prepared as described in Example I) in 2.0 milliliters of methanol was added 20 milligrams (2 eq) of camphorsulfonic acid and the resulting mixture was stirred at room temperature for three hours. An HPLC analysis ("ZORBAX", 45/55 A:B (containing 0.1% TFA) at 1.5 mL/min, at 40° C., λ=210 nm) showed completion of the reaction. The reaction mixture was injected directly onto a "ZORBAX" (25 mm×25 cm)C8 column and eluted with 50/50 A:B at 8.0 mL/min. Pure fractions as determined by HPLC were pooled and lyophilized to obtain 26 milligrams (58% yield) of the desired product Compound (A-I-15a) (Seq ID No. 41). HPLC analysis of the product indicated a purity of 96.1 percent.

$^1$H-NMR (400 MHz, CD$_3$OD): δ7.11 (d, 2H), 6.75 (d, 2H), 3.34 (s, 3H), 1.19 (d, 3H), 0.88 (t, 3H), 0.86 (d, 6H); Mass spectrum (FAB): 1072 (M+Li)

EXAMPLE IV

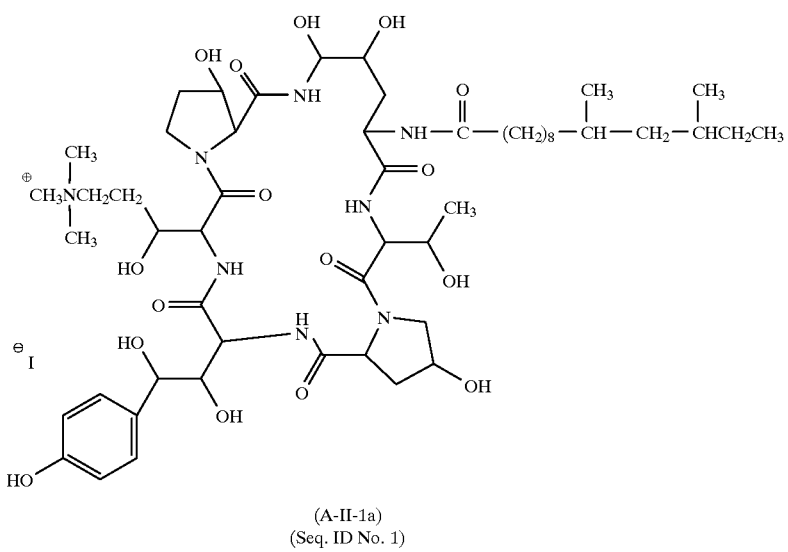

(A-II-1a)
(Seq. ID No. 1)

To a solution of 44 milligrams (42 μmol) of Compound A-I-1a (Seq. ID No. 1) (prepared as described in Example I) in 1.0 milliliter of sieve dried DMF (13×, 3A molecular sieves) was added 4.5 milligrams (53 μmol) of sodium bicarbonate, followed by 250 milligrams of 4A sieves and finally 26 microliters (417 μmol, 10 eq) of methyl iodide and the resulting solution was stirred at room temperature for 5 hours. At this time, 2.5 mg (30 μmol) of sodium bicarbonate and 26 microliters (417 μmol) of methyl iodide was added and the resulting mixture stirred overnight at room temperature. The reaction mixture was then applied directly to a preparative HPLC column and eluted with 55/45 A:B at 8.0 ml/min. Pure fractions as determined by HPLC were pooled and lyophilized to obtained 17 milligrams (37 percent yield) of Compound AII-1a (Seq ID No. 1). HPLC analysis indicated purity of 95.2 percent.

$^1$H-NMR (400 MHz, CD$_3$OD): δ7.11 (d, 2H), 6.73 (d, 2H), 5.16 (d, 1H), 4.98 (d, 1H), 3.16 (s, 9H), 1.19 (d, 3H), 0.88 (t, 3H), 0.85 (d, 6H); Mass Spectrum: (FAB): 1094 (M+H)

EXAMPLE V

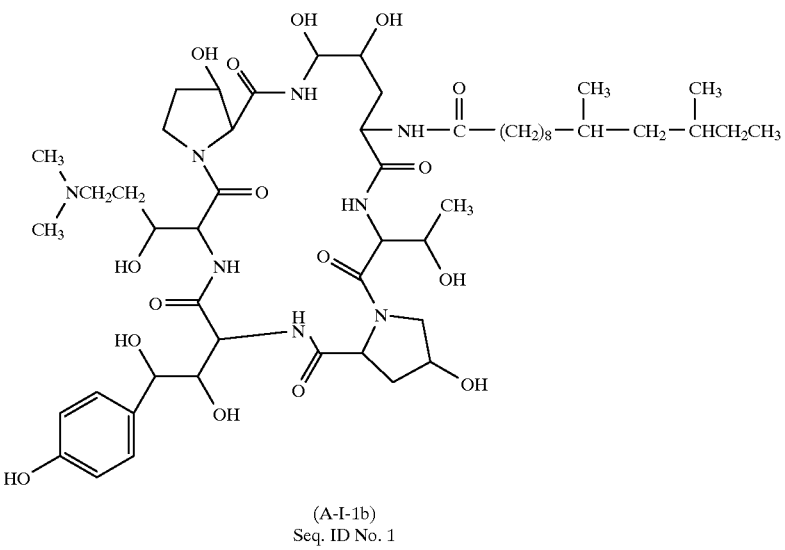

(A-I-1b)
Seq. ID No. 1

To a mixture of 0.262 gram (0.25 mmol) Compound A-I-1a (prepared as described in Example I) in 5 milliliters of acetonitrile containing 1 milliliter (12.5 mmol) of 37 percent aqueous formaldehyde is added 0.125 gram (2 mmol) of sodium cyanoborohydride and the mixture stirred at room temperature for 10 minutes. The mixture is then neutralized with acetic acid until the pH paper indicates neutrality. Acetonitrile is then added to precipitate the reaction product. The product is recovered by filtration, washed with ether and air dried. The product is purified by reverse phase chromatography using a "ZORBAX" C8 column and eluting with acetonitrile/water containing 0.1 percent acetic acid. Fractions containing the desired product, as determined by HPLC are combined, concentrated and lyophilized to obtain Compound A-I-1b (Seq. ID No. 1), the N,N-dimethyl product as an acetic acid salt. The molecular weight of the free base is 1078.

EXAMPLE VI

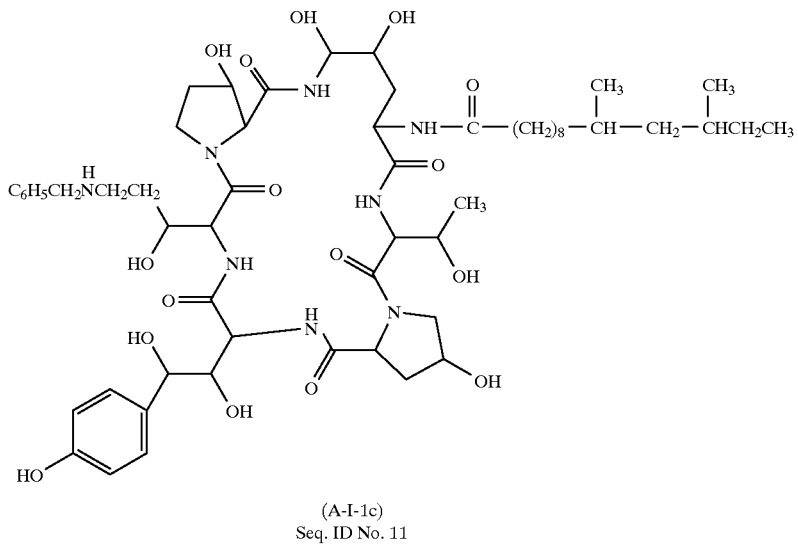

(A-I-1c)
Seq. ID No. 11

To a solution of 0.266 gram (0.25 mmol) Compound A-I-1a (Seq. ID No. 1) in 2.5 milliliters of methanol is added 0.132 gram (1.25 mmol) of benzaldehyde and the reaction mixture warmed to 60° C. for 15 minutes to obtain a Schiff base. The reaction mixture is allowed to cool to room temperature and the Schiff base precipitated with acetonitrile, filtered and resuspended in methanol. To the suspension is added 0.009 gram (0.25 mmol) of sodium borohydride and the mixture allowed to stir at room temperature until the solution is colorless. The excess reducing agent is then quenched with acetic acid and the product remaining in the reaction mixture is precipitated with acetonitrile, recovered and purified by reverse phase chromatography using "ZORBAX" C8 column and eluting with acetonitrile/water containing 0.1 percent acetic acid. Fractions containing the desired product as determined by HPLC are combined, concentrated and lyophilized to obtain the compound of formula A-I-1c (Seq. ID No. 1) as an acetic acid salt. The free base has a molecular weight of 1141.

EXAMPLE VII

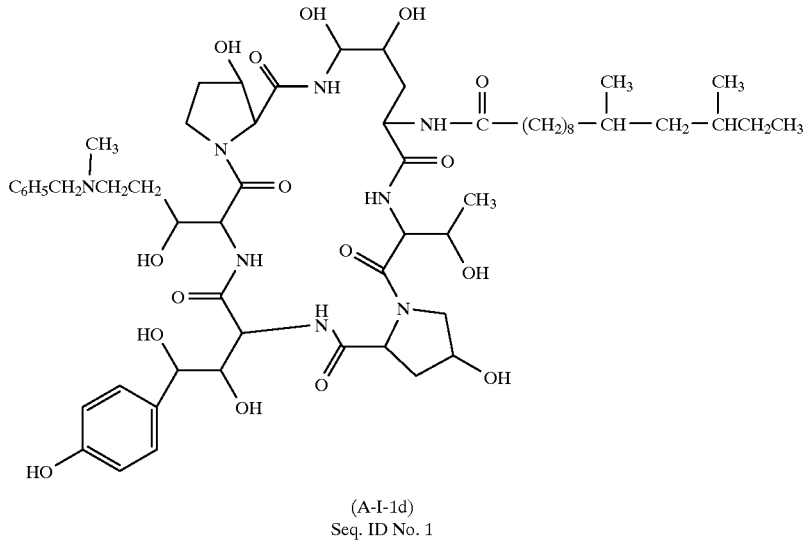

(A-I-1d)
Seq. ID No. 1

To a mixture of 0.142 gram (0.125 mmol) of N-benzyl compound of formula (A-I-1c) (prepared as described in Example VI) in 0.5 mL (6.25 mmol) of 37 percent aqueous formaldehyde is added 0.062 gram (1 mmol) of sodium cyanoborohydride and the mixture allowed to stir at room temperature for 1 hour. At the end of this period acetic acid is added until pH paper indicates neutrality. Acetonitrile is added to precipitate the desired N-methyl-N-benzyl product. The latter is recovered, washed with ether and air dried. The product is purified by reverse phase chromatography using a "ZORBAX" C8 column and eluting with acetonitrile/water containing 1 percent acetic acid. Fractions containing the desired product as determined by analytical HPLC are combined, concentrated and lyophilized to obtain N-methyl-N-benzyl derivative, Compound A-I-1d (Seq ID No. 1) as an acetic acid salt. The molecular weight of the free base is 1154.

EXAMPLE VIII

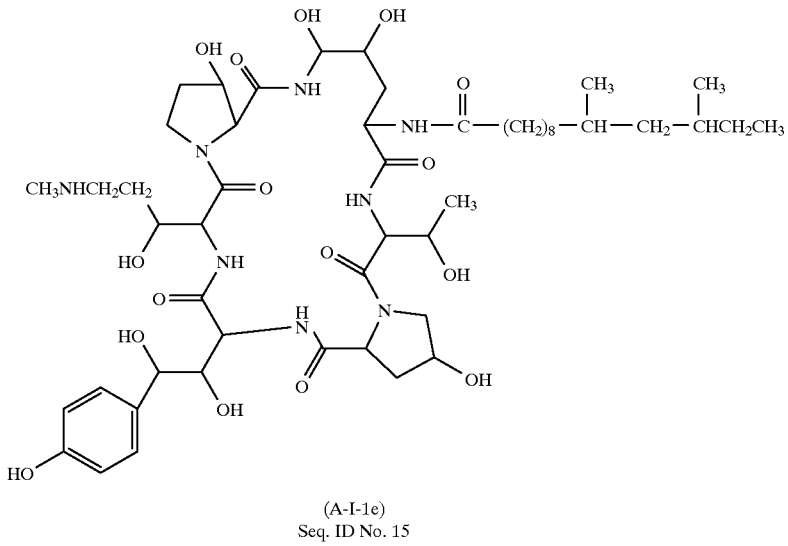

(A-I-1e)
Seq. ID No. 15

A solution of 0.072 gram (0.625 mmol) of N-methyl-N-benzyl derivative, Compound A-I-1d (Seq ID No. 1) in 1 milliliter of acetic acid is hydrogenated over 10 percent palladium on carbon catalyst (0.007 gram). After the starting material is consumed, the reaction mixture is flushed with nitrogen and the catalyst removed by filtration. The filtrate is concentrated and the residue purified by reverse phase chromatography using a "ZORBAX" C8 column eluting with acetonitrile/water containing 1 percent acetic acid. Fractions containing, as determined by analytical HPLC, the desired product are combined, concentrated and lyophilized to obtain N-methyl derivative Compound A-I-1c (Seq. ID No. 1) as the acetic acid salt. The molecular weight of the free base is 1141.

EXAMPLE IX

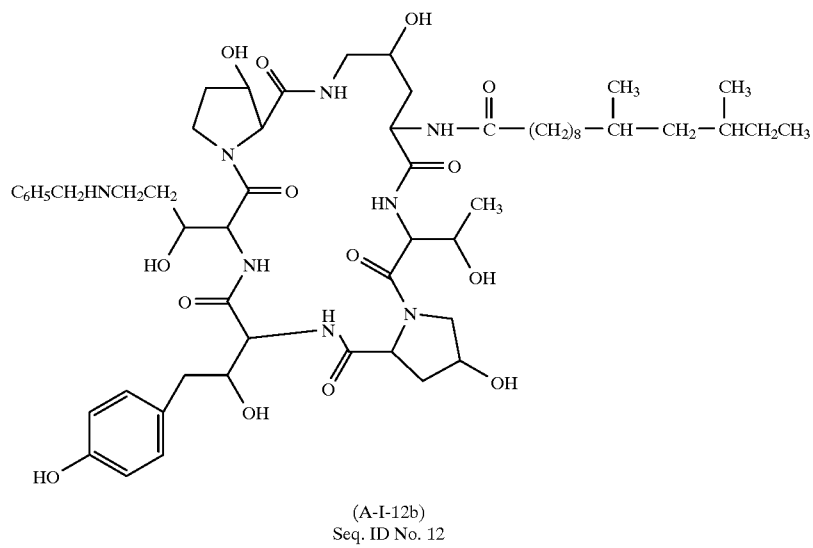

(A-I-12b)
Seq. ID No. 12

To a solution of 0.254 gram (0.25 mmol) of Compound A-I-12a (Seq ID No. 12 obtained as described in Example II)

is added 0.132 gram (1.25 mmol) of benzaldehyde and the reaction mixture warmed to 60° C. for 15 minutes. The mixture then is allowed to cool to room temperature and the resulting Schiff base isolated by precipitation with acetonitrile. The precipitate is recovered by filtration and resuspended in methanol. 0.009 gram (0.25 mmol) of sodium borohydride is added and the mixture allowed to stir at room temperature until the solution is colorless. Excess reducing agent is quenched with acetic acid and acetonitrile then added to precipitate the product. The latter is purified by reverse phase chromatography using "ZORBAX" C8 column eluting with acetonitrile/water containing 1 percent acetic acid. Fractions containing the desired product as determined by analytical HPLC are combined, concentrated and lyophilized to obtain the benzyl product Compound A-I-12b as an acetic acid salt. (Seq ID No. 12). Molecular weight of the free base is 1109.

EXAMPLE X

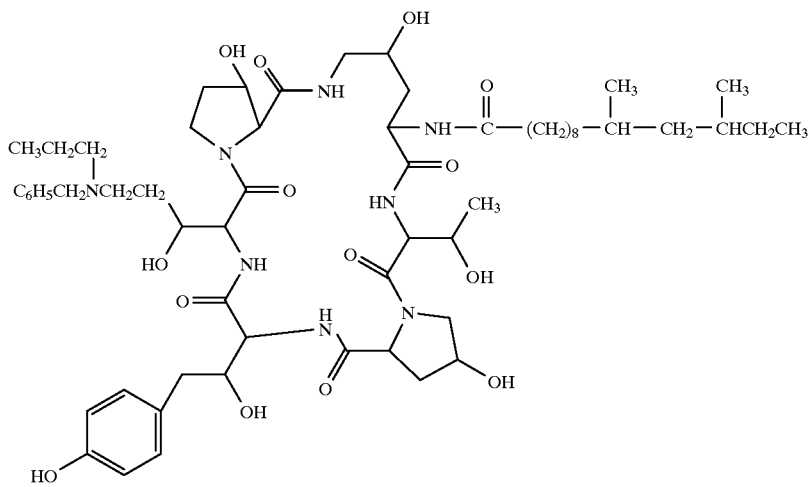

(A-I-12c)
Seq. ID No. 12

To a mixture of 0.138 gram (0.125 mmol) N-benzyl compound A-I-12b (Seq. ID No. 12) (prepared as described in Example IX) in 2.5 milliliters of acetonitrile and 1.0 milliliter of water containing 0.362 gram (6.25 mmol) of propionaldehyde is added 0.067 gram (1 mmol) of sodium cyanoborohydride and the mixture stirred at room temperature for 10 minutes. Acetic acid is then added to the mixture until neutral to pH paper. Acetonitrile is then added to precipitate the product which is filtered, washed with ether and air dried. The product is then purified by reverse phase chromatography using "ZORBAX" C8 column and eluting with acetonitrile/water containing 1 percent acetic acid. Fractions containing the desired product as determined by analytical HPLC are combined, concentrated and lyophilized to obtain N-benzyl-N-propyl Compound A-I-12c (Seq ID No. 12) as the acetic acid salt. The molecular weight of the free base is 1151.

EXAMPLE XI

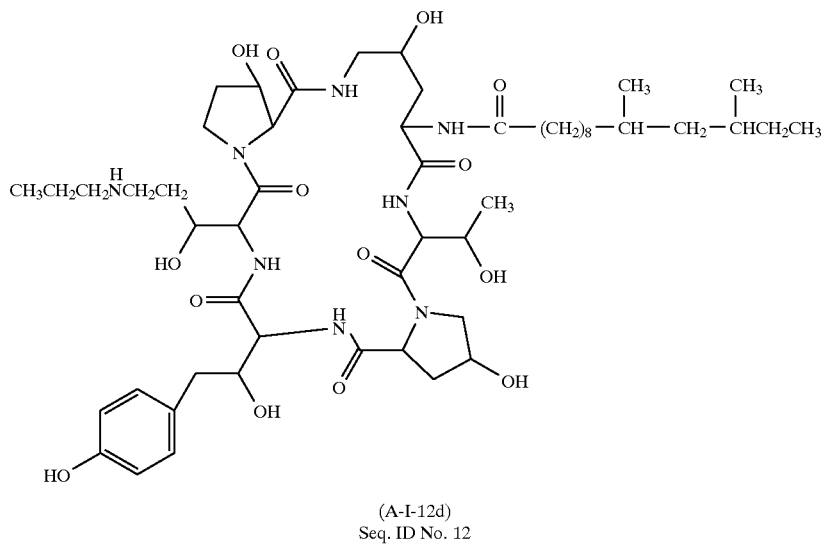

(A-I-12d)
Seq. ID No. 12

A solution of 0.143 gram (0.625 mmol) N-propyl-N-benzyl compound A-I-12c (Seq ID No. 12) prepared as described in Example X in acetic acid (1 milliliter) is hydrogenated over 10 percent palladium on carbon calatyst (0.007 gram). After the starting material is consumed, the reaction mixture is flushed with nitrogen and the catalyst removed by filtration. The filtrate is concentrated and the residue purified by reverse phase chromatography using "ZORBAX" C8 column eluting with acetonitrile water containing 1 percent acetic acid. Fractions containing the desired product as determined by analytical HPLC are combined, concentrated and lyophilized to obtain Compound A-I-12d as the acetic acid salt. The molecular weight of the free base is 1061.

EXAMPLE XII

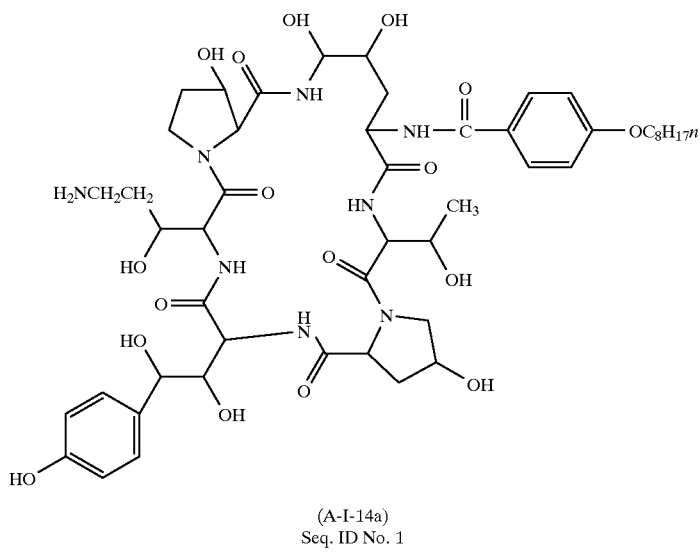

(A-I-14a)
Seq. ID No. 1

To a solution of 110 milligrams (0.104 mmol) of a lipopeptide compound ($R_1$, $R_2$, $R_3$ and $R_4$ are OH, $R_5$ is H, $R_6$ is $CH_3$ and $R^I$ is $C_6H_4OC_8H_{17}$) in sieve-dried DMF under an atmosphere of nitrogen was added 59 milligrams (0.322 mmol) of cyanuric acid in one portion. The reaction was allowed to proceed for 5.5 minutes and then quenched by the addition of 1.35 milliliters of 2M sodium acetate solution. HPLC analysis showed a product to starting material ratio of 15.5:1. The reaction mixture was diluted with 2.0 milliliters of 50 percent aqueous acetonitrile and injected onto a radial compression C18 Δ-Pak column (15μ, 100 A; 25 mm×50 cm). Elution was started at 12.0 mL/min. with 75:25 water/acetonitrile (0.1% TFA) until all the DMF and other front running materials had been eluted. The gradient was then stepped up to 50:50 over the course of 30 minutes and pure fractions of the product were collected, combined, and lyophilized to obtain 60 milligrams (55.5% yield) of product of >99.5% purity as determined by HPLC ("ZORBAX" C18; isocratic elution with 6:4 water/acetonitrile (0.1%

TFA) 1.5 mL/min.; 40° C.; γ210 nm; retention time=9.74 min.). The product had the following spectral characteristics:

$^1$H-NMR (400 MHz; $CD_3OD$) δ7.82 (d,2 H), 7.12 (d, 2 H) 6.94 (d, 2 H), 6.75 (d, 2 H), 5.37 (d, 1 H) 2.86 (dd, 1 H), 2.76 (dd, 1 H), 2.44 (m, 1 H), 2.29 (m, 1 H), 1.21 (d, 3 H), 0.9 (t, 3 H). Mass Spectrum (FAB) 1048 (M+Li)

To a solution of 73 milligrams (0.70 mmol) of the compound prepared above in 3.0 mL of methanol was added at room temperature 62 milligrams (0.476 mmol) of $CoCl_2·6H_2O$ and the mixture stirred until all of the cobalt salt had dissolved. 90 milligrams (2.38 mmol) of sodium borohydride was then added in four portions over the course of 5 minutes. A vigorous reaction took place with each addition. After five hours, the reaction was shown to be substantially complete by HPLC. The reaction was quenched by the addition of 1.33 milliliters of 2N HCl, and the mixture stirred until all of the dark color was discharged. The resulting solution was injected directly onto an HPLC column (radical compression C18 Δ pak; 15μ; 100 A, 25 mm×50 cm) and elution started at 12.0 mL/min with 75:25 water/acetonitrile (0.1% acetic acid) until all the front running colored material had been eluted. Then the gradient was stepped up to 70:30. The fractions were collected and the fractions containing product were combined and lyophilized to obtain 21 milligrams of pure product as the hydrochloride salt (>99.5% by HPLC, "ZORBAX" C18; isocratic elution 6:4 water/acetonitrile 1.5 mL/min; 40° C. λ=210 nm) HPLC retention time=6.46 minutes. The product had the following spectral properties:

$^1$H NMR (400 MHz, $CD_3OD$) δ7.82 (d, 2H), 7.12 (d, 2H), 6.96 (d, 2H), 6.75 (d, 2H), 5.27 (d, 1H), 5.10 (d, 1H), 2.45 (m, 1H), 2.29 (m, 1H), 1.21 (d, 3H), 0.9 (t, 3H). Mass Spectrum: (FAB) 1052 (M+Li)

EXAMPLE XIII

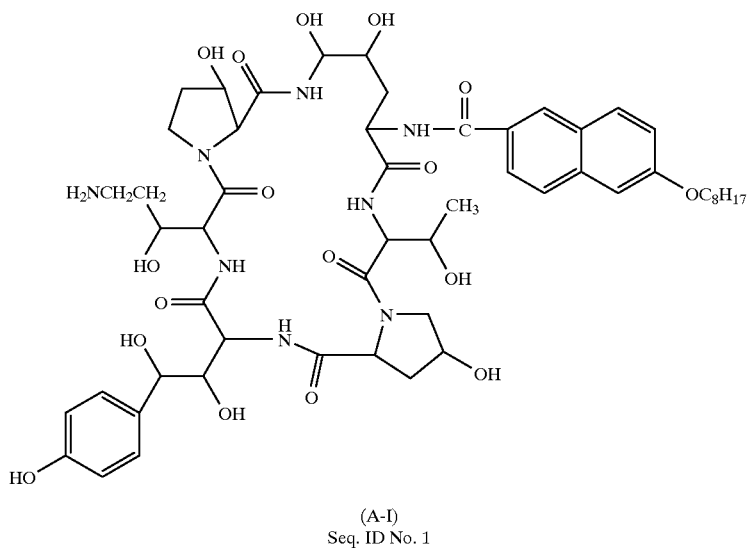

(A-I)
Seq. ID No. 1

In a manner similar to that described in Example XII, Compound A-I-14a (Seq ID No. 1) ($R_1$–$R_4$=OH, $R_5$ H, $R_6$=$CH_3$ $R^I$=$C_{10}H_6OC_8H_{17}$) having a molecular weight of 1095 as the free base may be prepared.

EXAMPLE XIV 1000 compressed tablets each containing 500 mg of Compound A-I-1a are prepared from the following formulation:

| Compound | Grams |
|---|---|
| Compound A-I-1a | 500 |
| Starch | 750 |
| Dibasic calcium phosphate, hydrous | 5000 |
| Calcium stearate | 2.5 |

The finely powdered ingredients are mixed well and granulated with 10 percent starch paste. The granulation is dried and compressed into tablets.

EXAMPLE XV 1000 hard gelatin capsules, each containing 500 mg of Compound A-1-12a are prepared from the following formulation:

| Compound | Grams |
|---|---|
| Compound AI-12a | 500 |
| Starch | 250 |
| Lactose | 750 |
| Talc | 250 |
| Calcium stearate | 10 |

A uniform mixture of the ingredients is prepared by blending and used to fill two-piece hard gelatin capsules.

EXAMPLE XVI

An aerosol composition may be prepared having the following formulation:

|  | Per Canister |
| --- | --- |
| Compound AII-1a | 24 mg |
| Lecithin NF Liquid Concentrated | 1.2 mg |
| Trichlorofluoromethane, NF | 4.026 g |
| Dichlorodifluoromethane, NF | 12.15 g |

EXAMPLE XVII 250 milliliters of an injectible solution may be prepared by conventional procedures having the following formulation:

| Dextrose | 12.5 g |
| --- | --- |
| Water | 250 ml |
| Compound AII-1a | 400 mg |

The ingredients are blended and thereafter sterilized for use.

EXAMPLE XVIII

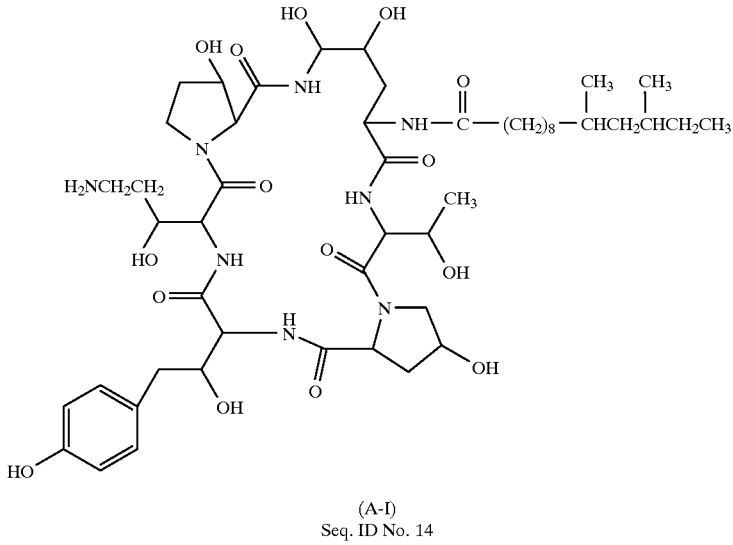

(A-I)
Seq. ID No. 14

To a solution 326 mg (0.3 mmol) of the product made in Example I as its hydrochloride addition salt in TFA (3.25 mL) was added Na(OAc)$_3$BH(636 mg, 3.0 mmol, 10 eq). The reaction mixture was stirred for two minutes at room temperature and then quenched by the addition of water (14 mL). Acetonitrile (1 mL) was added to bring everything into solution. The solution was divided up into three batches and injected onto two ZORBAX 25 mm×25cm C8 columns in series. Elution was performed with 55/45 H$_2$O/CH$_3$CN both 0.1% TFA at 20 mL/min. The various fractions were collected and analyzed by HPLC. The pure fractions were combined and lyophilized to afford 100 mg (29%) of the pure product (>96.0% by HPLC: 4.6 mm×25 cm ZORBAX C8; isocratic elution with 45/55 H$_2$O/CH$_3$CN both 0.1% TFA; flow rate=1.5 mL/min; temperature=40° C.; λ=210 nm; HPLC retention time=6.44 min); 400 MHz $^1$H NMR (CD$_3$OD) δ7.00 (d, 2 H), 6.70 (d, 2 H), 5.21 (d, 1 H), 4.98 (d, 1 H), 4.45 (m, 1H), 2.65 (m, 1 H), 2.47 (m, 1 H), 1.80 (m, 1H), 1.18 (d, 3H). Mass Spectrum (FAB): 1035 (M+H)

Preparation of Starting Materials

The starting materials for the compounds are natural products or derivatives of natural products.

The following compounds are natural products produced by cultivating an appropriate organism in nutrient medium as hereinafter described.

E-1 may be produced by cultivating *Zalerion arboricola* ATCC 20868 in a nutrient medium enriched in mannitol as the primary source of carbon as described in U.S. Pat. No. 5,021,341, Jun. 4, 1991.

E-2 may be produced by cultivating *Zalerion arboricola* ATCC 20868 in nutrient medium as described in U.S. Pat. No. 4,931,352, Jun. 5, 1990 or in nutrient medium enriched in glycerol as described in U.S. Pat. No. 4,968,608, Nov. 6, 1990.

E-2 nucleus with a different R may be produced by cultivating *Acrophialphora limonispora* in nutrient medium as described in U.S. Pat. No. 4,173,629.

E-3, E-10 and E-11 may be produced by cultivating Cryptosporiopsis ATCC 20594 in nutrient medium as described by Pache et al in 13th ICC (1983), PS 4.8/3, Part 115, Abstract No. 10 and PCT WO 82/00587.

E-4, E-5 and E-6 may be produced by cultivating *Zalerion arboricola* ATCC 20868 in nutrient medium.

E-7 may be produced by cultivating *Zalerion arboricola* ATCC 20958 in nutrient medium as described in U.S. Pat. No. 5,021,403.

E-8 may be produced by cultivating *Zalerion arboricola* ATCC 20958 in nutrient medium.

E-9 may be produced by cultivating *Zalerion arboricola* ATCC 74030 in nutrient medium.

Starting materials which are cyclohexapeptides in which the nucleus of the foregoing has been modified to produce novel hexapeptides in which R$_3$ or both R$_3$ and R$_1$ are hydrogen instead of hydroxyl may be obtained by intimately mixing a compound in which R$_3$ is hydroxyl and R$_1$ may be hydroxyl with a reducing agent such as sodium cyanoborohydride in the presence of a strong acid such as trifluoroacetic acid and the mixture stirred until the reaction is complete. The volatiles are then removed under reduced pressure and the residue purified by reverse phase chromatography employing water/acetonitrile to obtain a purified product. When $R_1$ is OH and it is desired to reduce only $R_3$, essentially the same procedure is used except that the reactant lipopeptide is first dissolved in glacial acetic acid and the reaction carried out in a similar manner. A compound in which $R_1$ and $R_3$ are H, and $R_2$ and $R_4$ are OH, $R_5$ is H and $R_6$ is $CH_3$ may be identified as E-12 and a compound in which $R_3$ is H and $R_1$, $R_2$ and $R_4$ are OH, $R_5$ is H and $R_6$ is $CH_3$ may be identified as E-13.

Starting materials in which $R'$ is a different group from that of the natural product may be obtained by deacylating the lipophilic group of the natural product by subjecting the natural product in a nutrient medium to a deacylating enzyme until substantial deacylation occurs, said enzyme having first been obtained by cultivating a microorganism of the family Pseudomondaceae or Actinoplanaceae, as also described in Experentia 34, 1670 (1978) or U.S. Pat. No. 4,293,482, and thereafter recovering the deacylated cyclopeptide, and acylating the deacylated cyclopeptide by mixing together with an appropriate active ester $R'COX$ to obtain Compound E with the desired acyl group as also described in U.S. Pat. No. 4,287,120 and 4,293,489.

When $R_1$ is H, $R_2$, $R_3$ and $R_4$ are OH, $R_5$ is H or $CH_3$ and $R_6$ is $CH_3$, starting material E, the nitrile intermediate may be made using another starting material, nitrile compound, or amine compound in which $R_1$ is OH with the remaining $R_5$ being the same, and reducing $R_1$ by methods known to the skilled in the art. Conveniently this may be carried out by adding trifluoroacetic acid to the material and triacetoxyborohydride and mixing together to obtain a product and thereafter purifying the product by conventional methods such as by HPLC.

What is claimed is:

1. A compound selected from the group consisting of:

(A) an amine represented by the formula (Seq. ID Nos. 1–13, 40 and 41)

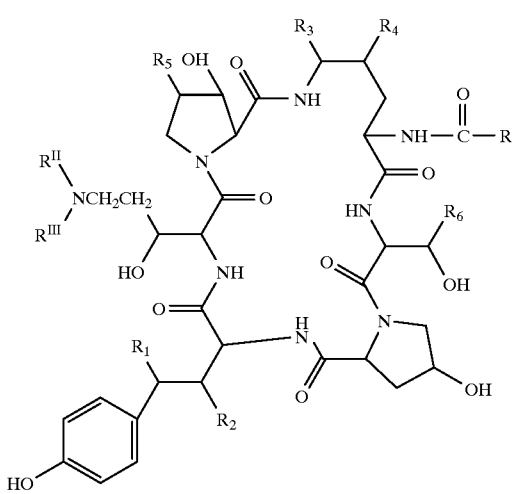

or its acid addition salt, and (B) a quaternary ammonium salt represented by the formula: (Seq. ID Nos. 1–13, 40 and 41)

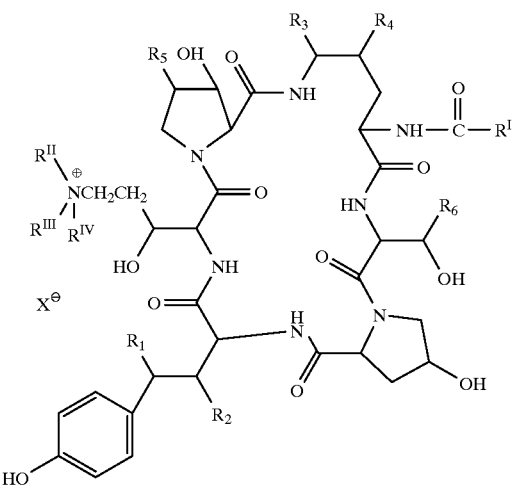

wherein
$R_1$ is H or OH
$R_2$ is H or OH
$R_3$ is H, OH or OR where R is $C_1$–$C_4$ alkyl or benzyl
$R_4$ is H or OH
$R_5$ is H,
$R_6$ is H or $CH_3$ $R^I$ is $C_9$–$C_{21}$ alkyl, $C_9$–$C_{21}$ alkenyl, or $C_1$–$C_{10}$ alkoxyphenyl; or $C_1$–$C_{10}$ alkoxynaphthyl;

$R^{II}$ is H, $C_1$–$C_4$ alkyl or benzyl;

$R^{III}$ is H, $C_1$–$C_4$ alkyl or benzyl or $R^{II}$ and $R^{III}$ together are $(CH_2)_{4-6}$;

$R^{IV}$ is $C_1$–$C_4$ alkyl; and

X is an anion of a pharmaceutically acceptable salt.

2. A compound according to claim 1 having the formula:

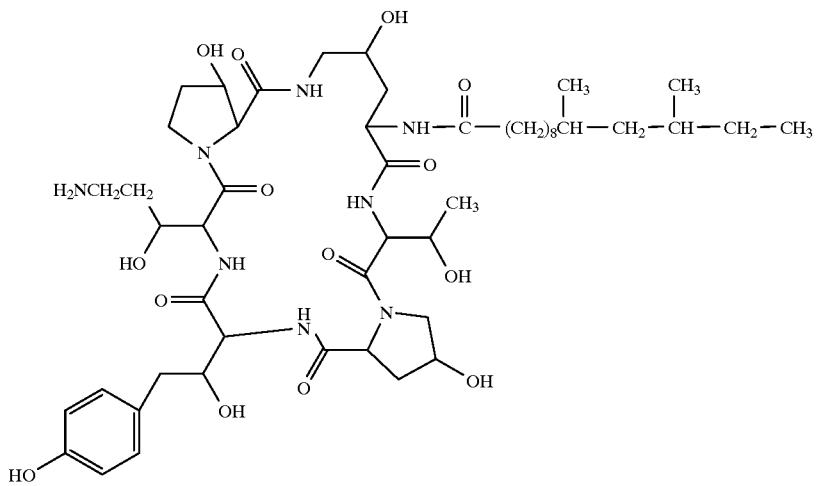

3. A compound according to claim 1 having the formula:

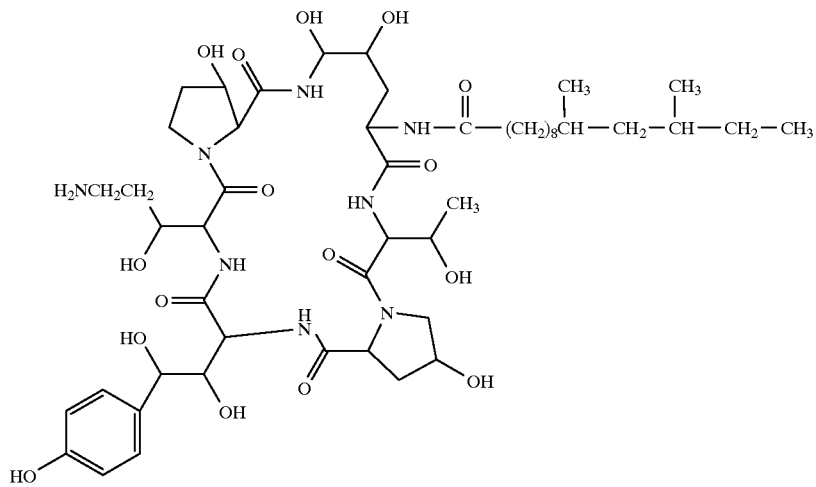

4. A compound according to claim 1 having the formula:
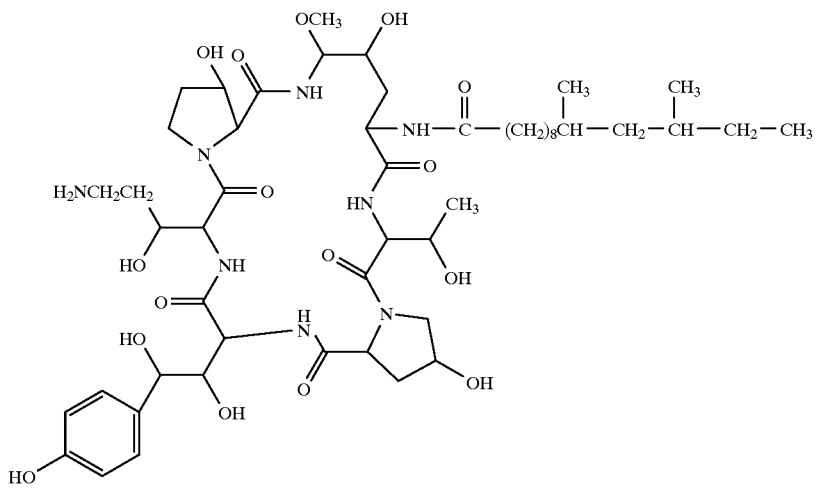
5. A compound according to claim 1 having the formula:
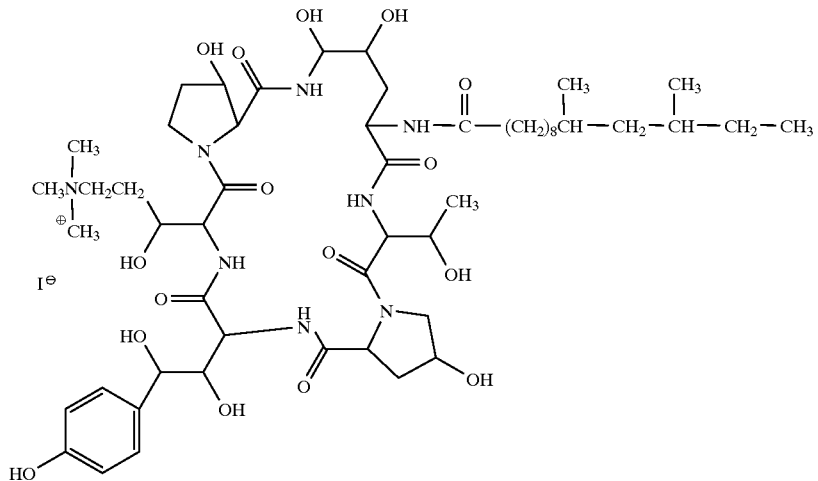

6. A compound of the formula:

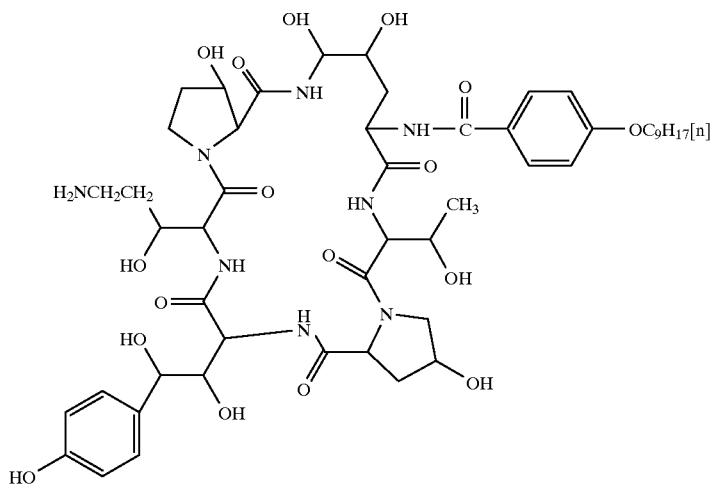

7. An antibiotic composition comprising an antimicrobial amount of a compound of claim 1 in a pharmaceutically acceptable carrier.

8. A composition according to claim 7 in unit dosage form wherein the compound is present in an amount of 100 mg to 200 mg.

9. A method of treating mycotic infections in a mammal in need of such treatment comprising administering an antimycotic effective amount of a compound of claim 1 to said mammal.

10. A compound according to claim 1 having the formula

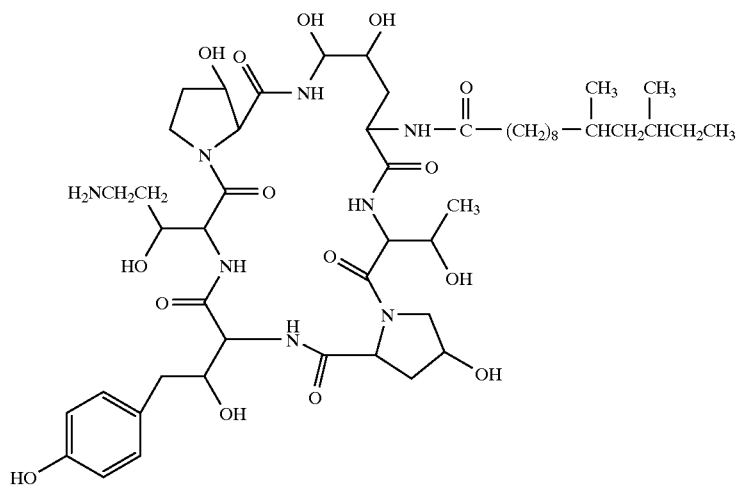

* * * * *